United States Patent
Anderson et al.

[11] Patent Number: 5,879,294
[45] Date of Patent: Mar. 9, 1999

[54] TISSUE CHROMOPHORE MEASUREMENT SYSTEM

[75] Inventors: David L. Anderson, Bloomington; Galen D. Houk; Mark S. Lewandowski, both of Hutchinson; Dean E. Myers, Stewert; Joseph P. Ortner, Hutchinson, all of Minn.

[73] Assignee: Hutchinson Technology Inc., Hutchinson, Minn.

[21] Appl. No.: 672,625

[22] Filed: Jun. 28, 1996

[51] Int. Cl.$^6$ .................................................. A61B 5/00
[52] U.S. Cl. ........................ 600/310; 600/323; 600/473; 600/476
[58] Field of Search ................ 128/63.3, 664, 128/665, 666; 356/39, 40, 41; 600/310, 322, 323, 473, 476, 479

[56] References Cited

U.S. PATENT DOCUMENTS

| | | | |
|---|---|---|---|
| 3,638,640 | 2/1972 | Shaw | 128/2 R |
| 3,811,777 | 5/1974 | Chance | 356/73 |
| 3,825,342 | 7/1974 | Lubbers et al. | 356/41 |
| 4,086,915 | 5/1978 | Kofsky et al. | 128/2 L |
| 4,223,680 | 9/1980 | Jöbsis | 128/633 |
| 4,281,645 | 8/1981 | Jöbsis | 128/633 |
| 4,380,240 | 4/1983 | Jöbsis et al. | 128/633 |
| 4,513,751 | 4/1985 | Abe et al. | 128/666 |
| 4,805,623 | 2/1989 | Jöbsis | 128/633 |
| 4,907,876 | 3/1990 | Suzuki et al. | 356/41 |
| 5,103,829 | 4/1992 | Suuki et al. | 128/633 |
| 5,127,408 | 7/1992 | Parsons | 128/634 |
| 5,197,470 | 3/1993 | Helfer et al. | 128/634 |
| 5,303,026 | 4/1994 | Strobl et al. | 356/318 |
| 5,355,880 | 10/1994 | Thomas et al. | 128/633 |
| 5,361,758 | 11/1994 | Hall et al. | 128/633 |
| 5,377,674 | 1/1995 | Kuestner | 128/633 |
| 5,482,034 | 1/1996 | Lewis et al. | 128/633 |
| 5,497,770 | 3/1996 | Morcos et al. | 128/633 |
| 5,533,509 | 7/1996 | Koashi et al. | 128/633 |
| 5,792,049 | 8/1998 | Eppstein et al. | 600/306 |

FOREIGN PATENT DOCUMENTS

| | | |
|---|---|---|
| 0 290 275 A1 | 11/1988 | European Pat. Off. . |
| 0 476 192 A2 | 3/1992 | European Pat. Off. . |
| 0 522 674 A2 | 1/1993 | European Pat. Off. . |

OTHER PUBLICATIONS

Biomedical Infared Spectroscopy by Jackson and Mantsch, Infrared Spectroscopy of Biomolecules, Chapter 11, pp. 311–340.

Jöbsis et al., "Reflectance Specteophotometry of Cytochrome aa$_3$ in vivo", J. Appl. Physiol.: Respirat. Environ. Exercise Physiol, Jan. 24, 1977, pp. 858–872.

(List continued on next page.)

Primary Examiner—Michael Peffley
Assistant Examiner—Eric F. Winakur
Attorney, Agent, or Firm—Faegre & Benson

[57] ABSTRACT

A measurement system and method for measuring a relative concentration of a first form of a chromophore having a first form and a second form. The method comprises irradiating a tissue sample with light at a plurality of wavelengths within a wavelength range within which the first and second forms of the chromophore provide an overlapping spectral response. A detector is provided that detects spectral data emitted from the tissue. Furthermore, the method comprises determining a first and a second 2d derivative spectrum value, at first and second wavelengths, respectively, within said wavelength range at which the first 2d derivative spectrum value varies with the relative concentration of the first form of the chromophore. A scaled, 2d derivative spectrum value is derived from the first and second 2d derivative spectrum values. A memory stores a correlation which provides the relative chromophore concentration as a function of the scaled, 2d derivative spectrum value. Finally, the relative concentration of the first form of the chromophore in the tissue sample is determined from the 2d derivative spectrum values and the correlation.

68 Claims, 25 Drawing Sheets

OTHER PUBLICATIONS

Ferrari et al., "Nonivasive Determination of Hemoglobin Saturation in Dogs by Derivative Near–Infrared Spectoscopy, American Journal of Physiology", vol. 256/No. 5, May 1989, pp. H1493–H1499.

Zdrojowski et al., "Optical Transmission and Reflection by Blood", IEEE, Transactions on Bio–Medical Engineering, vol. BME47, No. 2, Apr. 1970, pp. 122–128.

Sanderink et al., "Quantitative Measurement of Plasma Hemoglobin by Second Derivative Spectrophotometry", Clinica Chimica Acta, 146 (1985), pp. 65–73.

Fantini et al., "Quantitatve Determination of the Absorption Spectra of Chromophores in Strongly Scattering Media: A Light–Emitting–Diode Based Technique", Applied Optics, vol. 33, No. 22, Aug. 1, 1994, pp. 5204–5213.

Mochizuki et al., "Methods of Quantitating Cerebral Near Infrared", Oxygen Transport to Tissue X, pp. 183–189.

Wharton et al., "Studies on the Electron Transfer System", The Journal of Biological Chemistry, vol. 239, No. 6, Jun. 1964, pp. 2036–2041.

Elam et al., "Sources of Error in Oximetry", Annuals of Surgery, vol. 130, 1949, pp. 755–773.

Enson et al., "In Vivo Studies with an Intravascular and Intracardiac Reflection Oximeter", Journal of Applied Physiology, vol. 17, 1962, pp. 552–558.

Wood et al., "Photoelectric Determination of Arterial Oxygen Saturation in Man", Journal of Laboratory & Clinical Medicine, vol. 34, 1949 pp. 387–401.

Kuenstner et al., Measurement of Hemoglobin in Unlysed Blood by Near–Infrared Spectroscopy, Applied Spectroscopy, vol. 48, No. 4, 1994, pp. 484–488.

Matcher et al., Absolute Qualification of Deoxyhaemoglobin Concentration in Tissue Near Infrared Spectroscopy, Phys. Med. Biol. 39 (1994) pp. 1295–1312.

Ostrander, In Vivo Reflectance of Blood and Tissue as a Function of Light Wavelength, IEEE Transactions on Biomedical Engineering, vol. 37, No. 6, Jun. 1990, pp. 632–639.

Marx, Laser Spectroscopy Techniques Monitor Oxygen Levels in Blood, World News, May 1993, pp. 38–40.

Wray et al., Characterization of the Near Infrared Absorption Spectra of Cythoshrome $aa_3$ and Haemoglobin for the Non–invasive Monitoring of Cerebral Oxygenation, Viochemica et Biophysica Acta 933 (1988) pp. 184–192.

Piantadosi, Near Infrared Spectroscopy: Principles and Application to Noninvasive Assessment of Tissue Oxygenation, Journal of Critical Care, vol. 4, No. 4, Dec. 1989, pp. 308–318.

MELANIN ABSORBANCE SPECTRA AT 37 deg C
NO TRANSFORMATION OF X SCALE

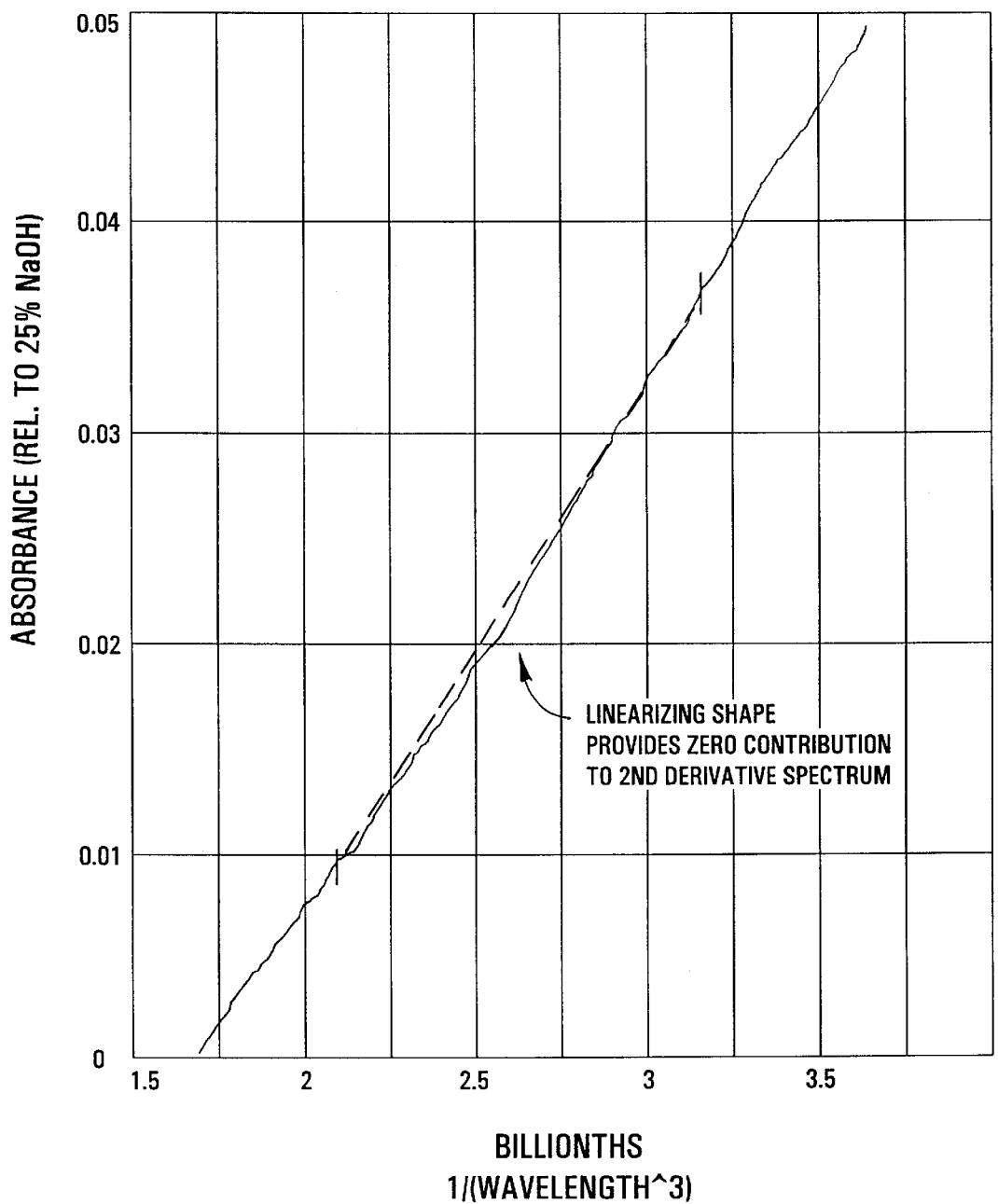

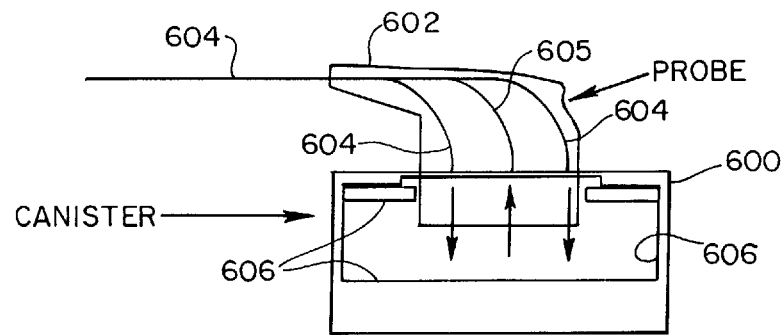
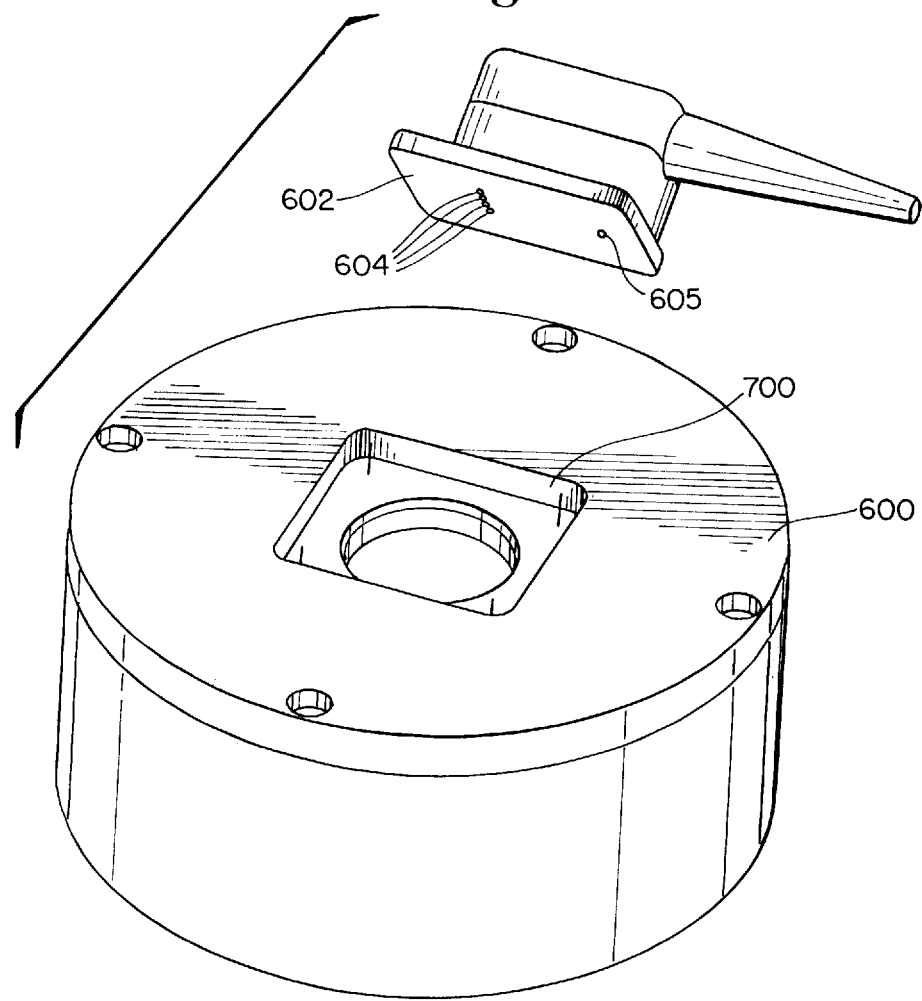

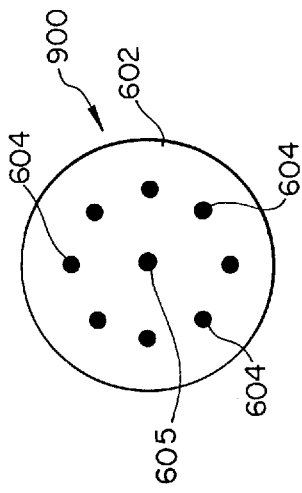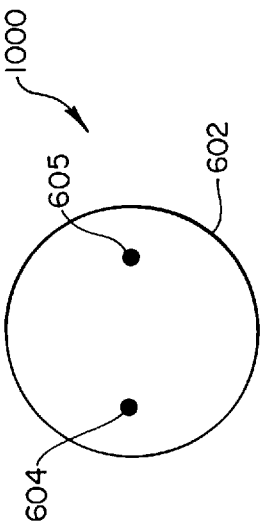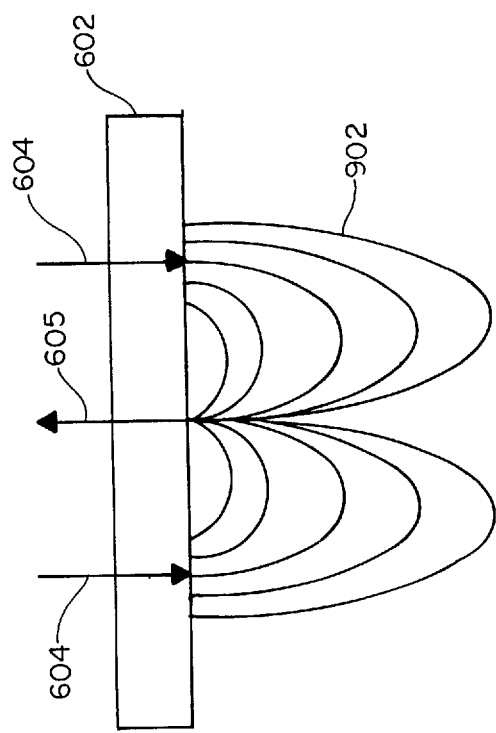

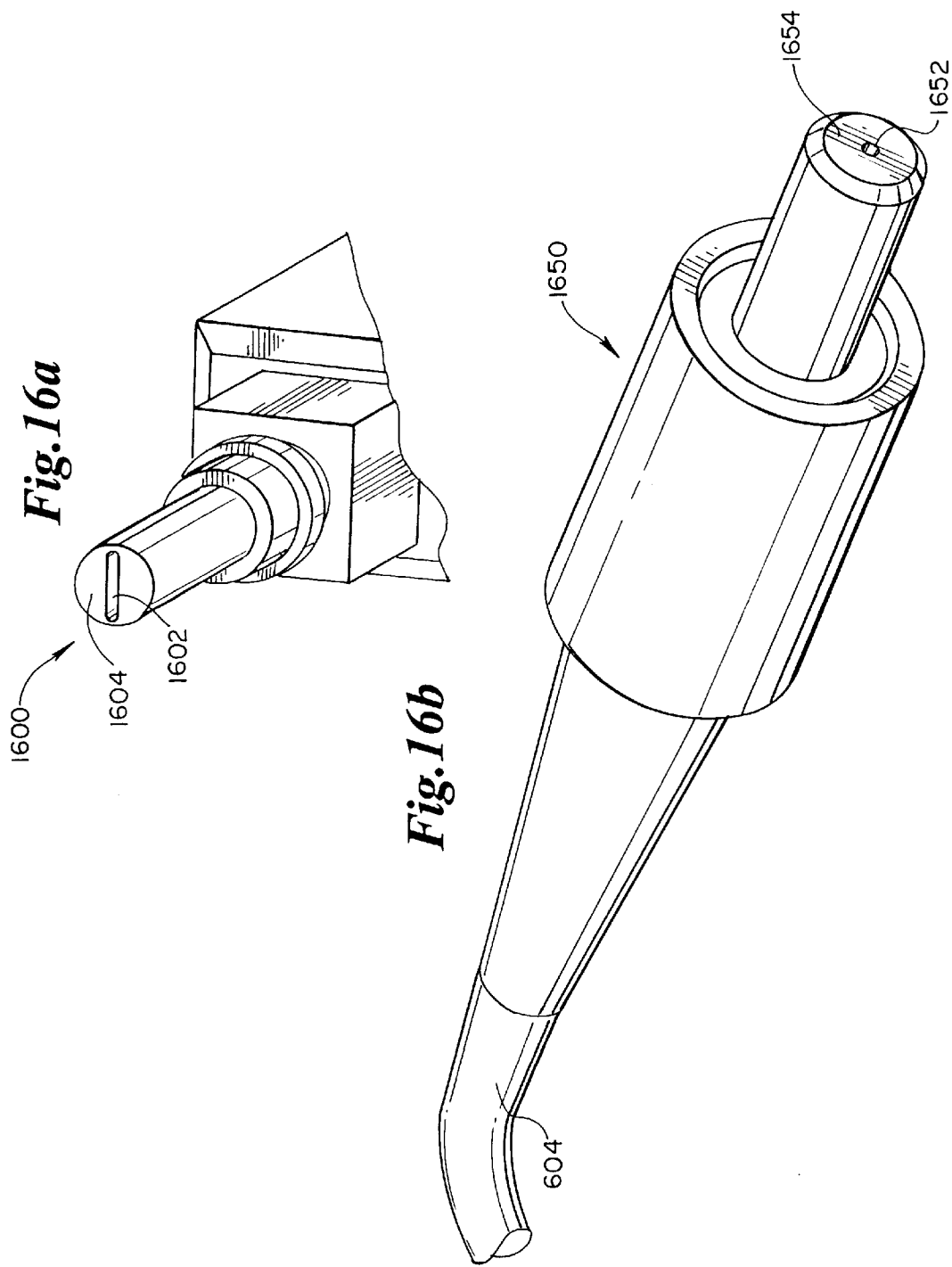

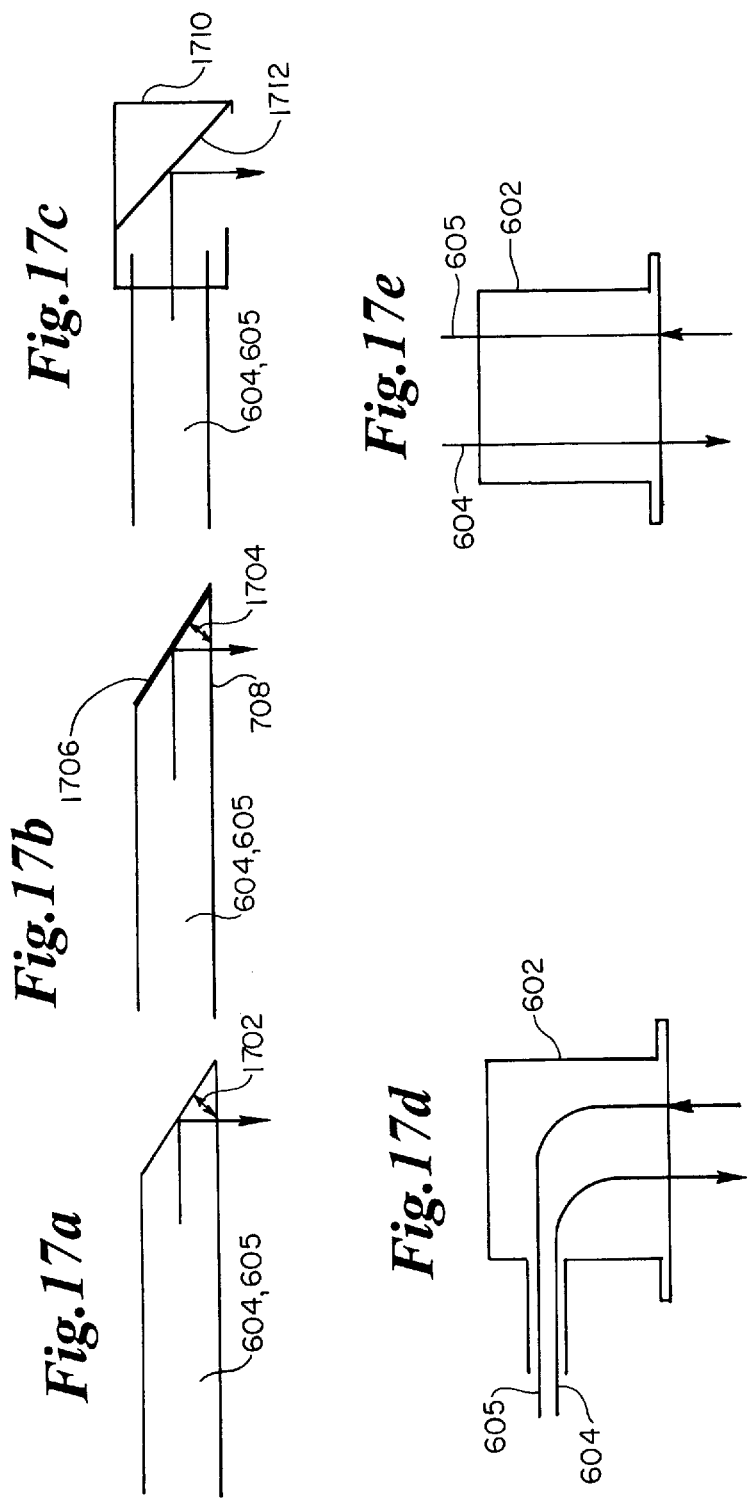

TISSUE CHROMOPHORE MEASUREMENT SYSTEM

BACKGROUND OF THE INVENTION

1. Field of the Invention

This invention relates generally to both a method and apparatus for the determination of a relative concentration of a first tissue chromophore with respect to a total concentration of a second, but related tissue chromophore. Specifically, the invention is a system for determining the concentration of oxyhemoglobin relative to the total concentration of hemoglobin within a blood-containing (blood perfused) tissue.

2. Description of the Related Art

Generally, when diagnosing the function of a body organ such as the cerebral tissues or the heart, the important parameters to measure are the oxygen quantity in the body organ and the organ's utilization of oxygen. Supplying body organs with a sufficient quantity of oxygen is also important for the growth of infants. An insufficiency of oxygen can affect many body organs.

Numerous apparatus and methods for examining the oxygen quantity in body organs readily and at various stages of illness are known in the art. For example, U.S. Pat. No. 4,281,645, issued Aug. 4, 1981 teaches the measurement of variations in oxygen quantity in body organs using apparatus in vivo to measure the absorption spectrum of near infrared light for the tissue of interest. In particular, the absorption is caused by the hemoglobin which is an oxygen-carrying medium in blood, and the cytochrome $a,a_3$ which performs an oxidation-reduction reaction in cells. The '645 patent discloses and teaches the use of four separate near infrared light rays having distinct wavelengths different from one another to determine the variation of cerebral oxygen quantity. The apparatus and techniques taught by the '645 patent utilize the relationship "Abs=a*l*c", where "Abs" is an optical absorption value, "a" is the empirically determined absorption coefficient for a particular chromophore, i.e. hemoglobin, "l" is the optical pathlength over which the radiated light travels, and "c" is the density or concentration of the chromophore of interest being measured. The system of the '645 patent produces an output signal representing the difference in or ratio of absorption of the measuring and reference wavelengths by the organ or other corporeal portion of the body as a function of the state of the metabolic activity in vivo, which may be converted to a signal providing a substantially continuous measure of such activity.

Other related techniques and apparatus have also been developed and are known. For example, U.S. Pat. No. 4,805,623, issued Feb. 21, 1989, to Jobsis, and entitled *Spectrophotometric Method For Quantitatively Determining The Concentration Of A Dilute Component In A Light Or Other Radiation-Scattering Environment*, teaches quantitatively determining the concentration of a dilute component in either a clear or a strongly light-scattering environment which also contains a reference component of known concentration. The method uses a series of contemporaneous radiation-directing and measurement steps of radiation of selected varying wavelengths. Thus, the method taught by Jobsis requires prior knowledge of the concentration of a reference component in order to determine the unknown concentration of the component of interest.

U.S. Pat. No. 5,139,025, issued Aug. 18, 1992, to Lewis et al., and entitled *Method And Apparatus For In Vivo Optical Spectroscopic Examination*, teaches clinical evaluation of biological matter, in particular human anatomy, examined in situ and in vivo, by selective spectral light transmissivity. The method and apparatus disclosed by Lewis et al. requires knowledge of conditioning factors in quantifying the resulting light-reception data, the conditioning factors consisting of relative geometrical locations and spacing of the light receivers and the nominal optical distance, and particularly the difference between the optical distance between the location of the near receptor, or receiver, and that of the far receptor or receiver.

Other methods and apparatus known in the art generally require knowledge of or precise measurement of the optical pathlength and/or empirical calculations of absorption coefficients for a component to be measured, or otherwise are useful only in providing trend data relating to the component of interest to be measured. One such example, U. S. Pat. No. 5,482,034, issued Jan. 9, 1996, to Lewis et al., and entitled *Method And Apparatus For Spectrophotometric Cerebral Oximetry And The Like*, teaches the processing of signals representative of the radiation detected by first and second receivers, to obtain data which particularly characterizes selected attributes of the measured substance within the particular internal region. The method and apparatus taught by the '034 patent requires precise placement of the first and second receivers with respect to one another.

Another technique is disclosed by S. J. Matcher and C. E. Cooper in *Absolute quantification of deoxyhemoglobin concentration in tissue near infrared spectroscopy*, Phys. Med. Biol. 39 (1994), 1295–1312. Matcher et al. teaches a method, using a suitable multi-wavelength NIR spectrometer to obtain an in vivo second-differential spectrum, and applies multi-linear regression to fit the acquired spectrum with the reference second-differential spectra of hemoglobin (Hb) and water ($H_2O$). The ratio of [Hb] to [$H_2O$] is then multiplied by the assumed concentration of water in the tissue to yield [Hb].

In view of the foregoing, a need in the art still exists for a method and apparatus suitable for providing accurate measurements relating to particular chromophores, but which is substantially robust to changes in optical pathlength and/or changes in total concentrations of specific chromophores to be measured. Preferably, such a method and apparatus will yield relative concentrations of a first chromophore, i.e. oxyhemoglobin with respect to the total concentration of a different, but related chromophore, i.e. hemoglobin, regardless of the total concentration of the related chromophore, and substantially unaffected by probe placement. The measurement apparatus should also be insensitive to the effects of scattering and interfering spectral contributors, e.g. melanin and bilirubin will not effect the accuracy of measurements.

Systems which measure the tissue chromophore of % oxyhemoglobin relative to total hemoglobin ($StO_2$) are known in the art and commercially available. For example, systems of this type are available from ISS of Champaign, Ill. and Somanetics of Troy, Mich. Specifically, the ISS device measures absolute tissue absorbance by correlating the phase shift between the send and receive signals of modulated monochromatic light at multiple wavelengths. This methodology allows for direct measurement of optical pathlength and measurement of tissue chromophores using absorbance measurements. The ISS device also correlates absolute absorbance to $StO_2$ using pure oxyhemoglobin and deoxyhemoglobin absorption coefficients. The absorption coefficients for mixtures of these two chromophores (values other than 0% and 100% $StO_2$) are assumed to be constant within the measurement range (Beer-Lambert Law). What is still needed is a method and apparatus that does not require measurement of optical pathlength, has reduced complexity, and eliminates pathlength sensitivity, all while offering more accurate measurements between 0% and 100% $StO_2$.

The Somanetics device measures tissue absorption values at two wavelengths within two different depths (two distinct send/receive spacings). The four absorption value measurements are empirically calibrated to $StO_2$ units using a brain tissue model. Calibration spectra is obtained from human forehead measurements at conditions where the blood saturation of the jugular vein is also measured. The calibration spectra is assigned $StO_2$ values calibrated from a weighted average of arterial and jugular vein measurements (field saturation). However, a field saturation measurement being an approximate estimate of tissue $StO_2$ does not always correlate with true tissue readings. What is still needed is a calibration set in which the spectral measurements are obtained at accurately known values. The Somanetics device is subject to scattering variations which can induce significant errors within the respective measurements.

SUMMARY OF THE INVENTION

The present invention addresses the need for a method and apparatus capable of non-invasively and in vivo, or alternatively, invasively, including but not limited to via catheterization, measuring a relative concentration of a first tissue chromophore with respect to a total concentration of a second, but related tissue chromophore within a tissue, including a tissue which may have physiological characteristics observed in blood-containing tissue, and which is capable of providing spectral measurements which are relatively immune to and unaffected by changes in optical pathlength and/or the total concentration levels of the related tissue chromophore. Further, the present invention addresses the long felt need to provide a method and apparatus of accurately measuring chromophore concentration levels in which the measurements are relatively unaffected by tissue scattering losses or by interfering spectral contributors including melanin and bilirubin.

In one embodiment, the aforementioned characteristics are achieved by providing a new system of measurement components in cooperation with an improved method of operation to yield the novel results. Accordingly, one characterization of the novel method and apparatus includes a measurement probe which irradiates the desired tissue with light transmitted from a broad bandwidth light source to determine spectral data over a spectral region of interest, most preferably within the 600 nm to 900 nm region for oxyhemoglobin and hemoglobin, for example. The probe is designed to be nonfluorescing and minimally reflecting, thereby increasing the accuracy of measurement for the transmitted light which emerges from the tissue of interest being examined. Another aspect of the inventive measurement probe allows the probe to operate over a particularly wide spectral region of interest without loss of accuracy or sensitivity, in contrast with probes generally used in the art which are useful only over specific and narrowly defined spectral regions.

Another aspect of the present measurement system includes use of a neural network having calibration characteristics for transforming the measured spectral data emerging from the tissue of interest into quantified signals representative of a concentration of oxyhemoglobin, for example, with respect to a total concentration of hemoglobin. The neural network performs comparison and transformation operations on the measured spectral data in which changes in the total concentration of hemoglobin, for example, and/or optical pathlength remain transparent and do not affect the accuracy of output data generated by the neural network.

In yet another aspect of the present invention, the method used to measure the spectral data is insensitive to tissue scattering effects and/or interfering spectral contributors including melanin and bilirubin.

BRIEF DESCRIPTION OF THE DRAWINGS

FIG. 2 depicts the same set of characteristic data as that shown in FIG. 1, but taken at different total concentration of the predetermined chromophore of interest;

FIG. 6 is a graph which illustrates a suitable nonlinear transformation of the wavelength axis for the scattering losses and/or interfering spectral contributors depicted in FIG. 5 in which the nonlinear transformation minimizes the measurement errors of the predetermined chromophore(s);

FIG. 7 illustrates a simplified pictorial of a reference canister which allows measurements of a desired light source spectrum without distorting and/or adding bias to the spectral shape of the measured spectrum;

FIG. 8 illustrates one preferred embodiment for the reference canister depicted in FIG. 7;

FIGS. 10a–10b illustrate a simplified diagram for a light probe tip suitable to act as an interface between predetermined send/receive optical light fibers and a predetermined measurement media (i.e. tissue);

FIGS. 10c–10d illustrate yet another simplified diagram for a light probe tip suitable to act as an interface between predetermined send/receive optical light fibers and a predetermined measurement media (i.e. tissue);

FIG. 16a illustrates one preferred embodiment for a receive connector plug assembly having optical fibers arranged in a slit pattern, suitable for transmitting light emitted from a predetermined tissue for transmission to a wavelength detector (array spectrometer);

FIG. 16b illustrates one preferred embodiment for a transmit connector plug assembly having at least one optical fiber, suitable for transmitting light emitted from a predetermined light source to irradiate a tissue;

FIGS. 17a–17e illustrate different optical fiber configurations which are suitable for use with the present measurement system;

DETAILED DESCRIPTION OF THE PREFERRED EMBODIMENTS

Figure 1:
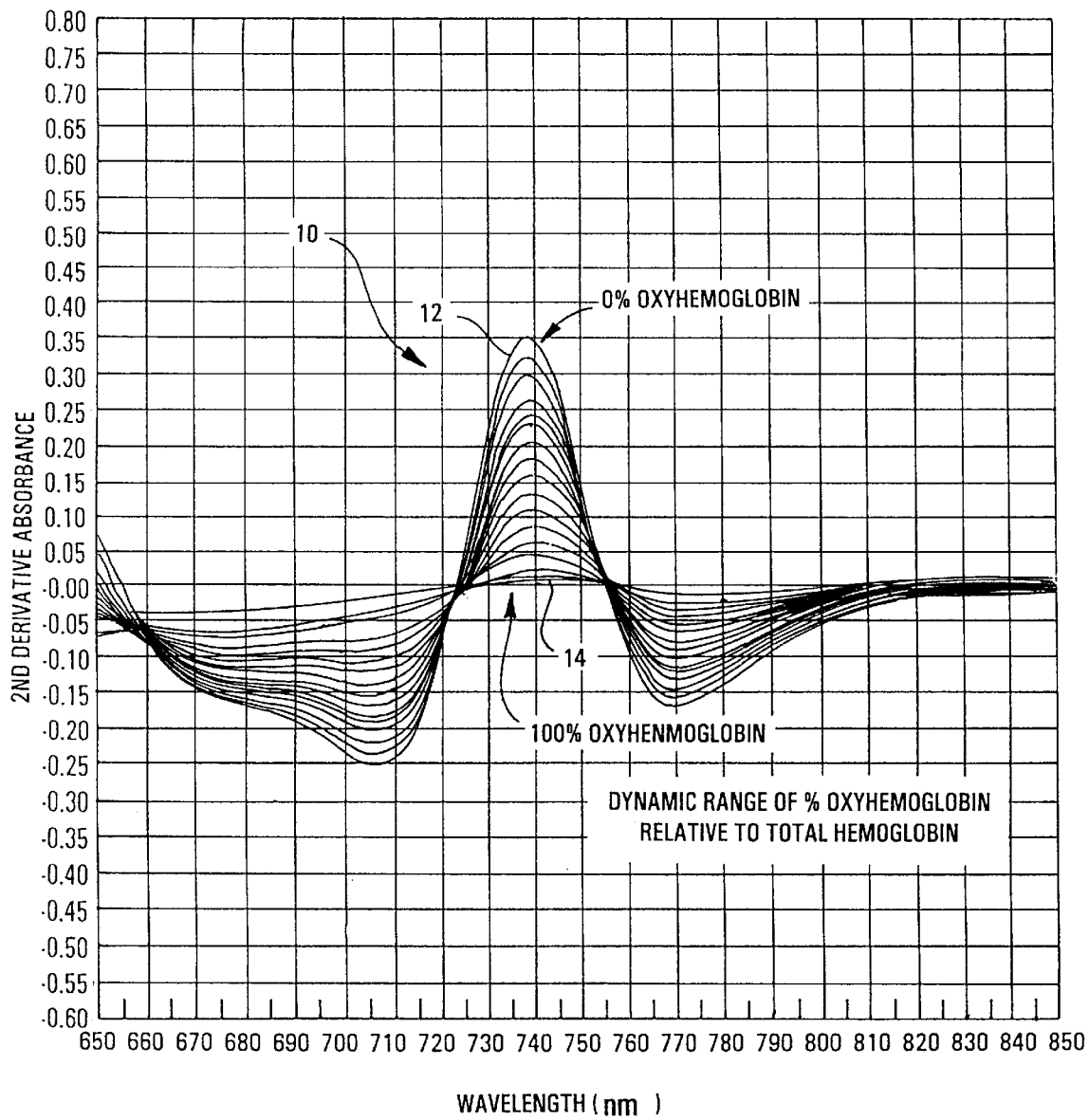
FIG. 1 is a graph which illustrates how changing the relative concentration of a predetermined chromophore through a predetermined tissue having physiological characteristics observed in blood-containing tissue affects the second derivative absorbance spectra characterized over a desired spectral region of interest for the predetermined chromophore.

The present invention can be described with reference to the various Figures of the drawings, FIG. 1 showing generally the effects of changing relative concentration on spectral data for a chromophore in interest. In the instant case, a preferred embodiment will be described as it relates to measuring concentrations of oxyhemoglobin as a percentage of total concentration of hemoglobin within a blood-containing tissue of interest. It shall be understood that a blood-containing tissue, as referenced hereinafter, will include any tissue perfused with blood, or even blood itself, which is also a tissue. The present invention is not so limited however, and it will be readily apparent to those of skill in the art of chromophore measurement, that the present inventive apparatus and methods are also useful for obtaining chromophore measurement data for non-blood perfused tissue when it is desirable to examine chromophores which are or may be present in such non-blood perfused tissue.

Referring now to FIG. 1, a family of spectral data 10 illustrate spectral characteristics for different relative concentrations of oxyhemoglobin measured over a spectral region of interest, such spectral region being 650 nm to 850 nm in the instant case. For example, it can be seen that the spectral characteristics displayed by the spectral data 12, which was measured for 0% concentration of oxyhemoglobin are substantially and visually different from the spectral characteristics displayed by the spectral data 14, which was measured for 100% relative concentration of oxyhemoglobin. Such characteristics are well known to those skilled in the art of chromophore measurement. Many methods and apparatus known in the art are limited in scope to measuring solely the concentrations of a specific chromophore, i.e. oxyhemoglobin, at 0% and 100% relative concentrations. The present invention differs from those known methods and apparatus by utilizing data taken from spectral characteristics for the particular chromophore, measured over the spectral region of interest, and for a family of differing concentrations lying between the outer limits of 0% and 100% concentration levels. Such a family of spectral data 10 are depicted in FIG. 1, and can be seen to retain a substantially consistent type of pattern for oxyhemoglobin, regardless of the relative concentration level of oxyhemoglobin. As FIG. 1 illustrates, the family of spectral data 10 are sensitive to changes in the relative concentration of oxyhemoglobin. Such a family of data 10 can be generated at conditions of variable optical pathlength and/or total chromophore concentration. A technique for increasing or decreasing the optical pathlength is to alter the distance between the light source (at the point of radiation transmission closest to the tissue being irradiated) used to irradiate the tissue and the light detector (at the point to radiation detection closest to the tissue being irradiated) used to measure the light emerging from the tissue.

Figure 2:
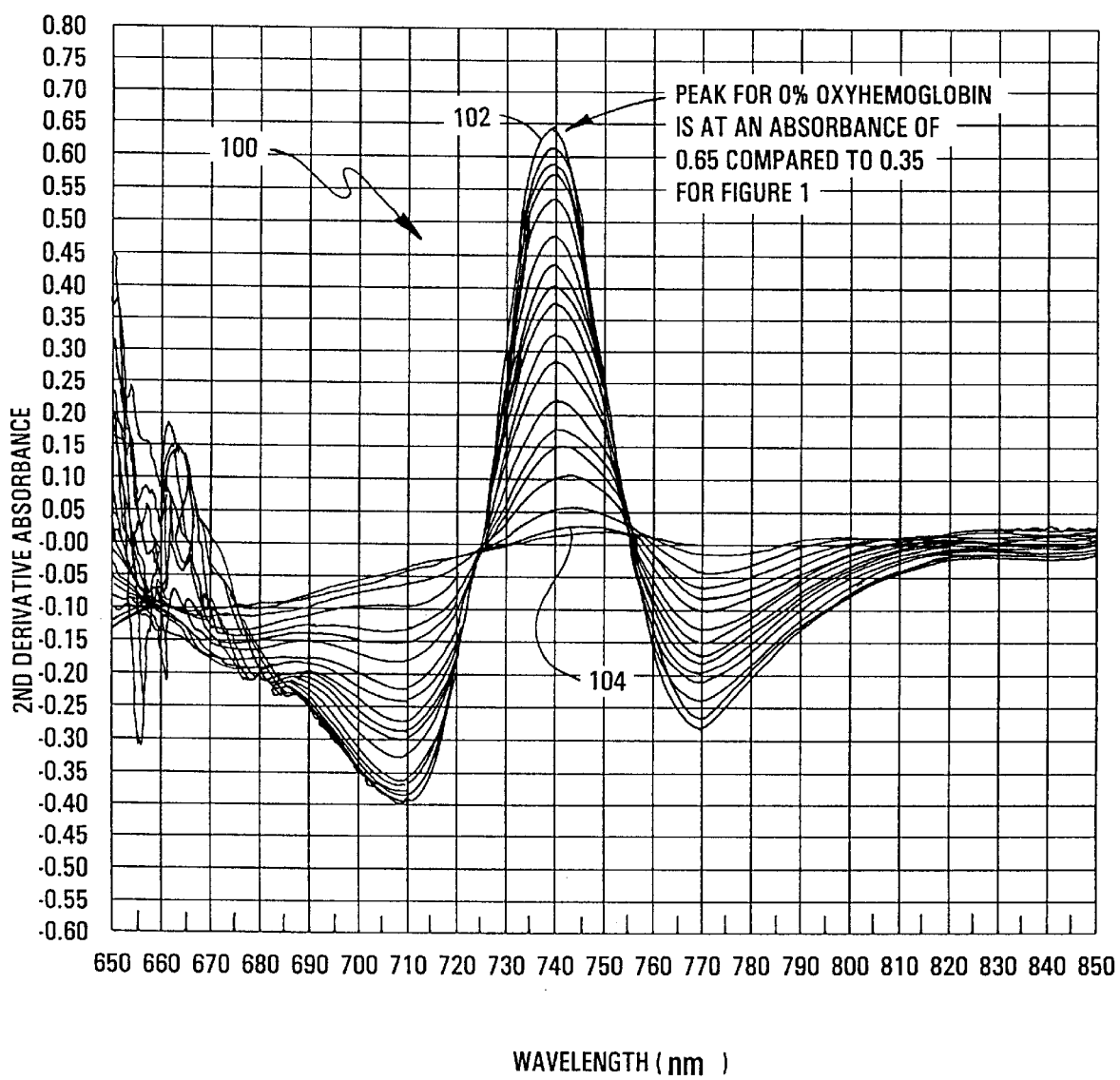
FIG. 2 is a graph which illustrates the effects on measurement range of the second derivative absorbance spectra from a change in the total concentration of a predetermined chromophore through a predetermined tissue having physiological characteristics observed in blood-containing tissue.

Turning now to FIG. 2, yet another family of spectral data 100 are shown which illustrate the effects on the family of spectral data 10 depicted in FIG. 1, by changes in the total concentration level of hemoglobin. A similar family of spectral data 100 could have been obtained by changing optical pathlength rather than total concentration level of hemoglobin. For example, it can be seen in FIG. 2 that altering the total concentration of hemoglobin in the instant case results in a family of spectral data 100 in which the spectral characteristics of oxyhemoglobin have now effectively been dispersed over a wider range of amplitude values. In the instant case, the spectral value for 0% relative concentration of oxyhemoglobin went from approximately 0.35 nominal amplitude in FIG. 1 to approximately 0.64 nominal amplitude in FIG. 2. Although the spectral characteristics for 100% relative concentration of oxyhemoglobin were substantially altered, the spectral value at a wavelength of 740 nm changed only slightly from about 0.01 nominal amplitude in FIG. 1 to about 0.015 nominal amplitude in FIG. 2. Thus, it can be seen that the spectral characteristics of oxyhemoglobin change more drastically with changes in total hemoglobin concentration as the relative concentration of oxyhemoglobin is reduced.

Figure 3:
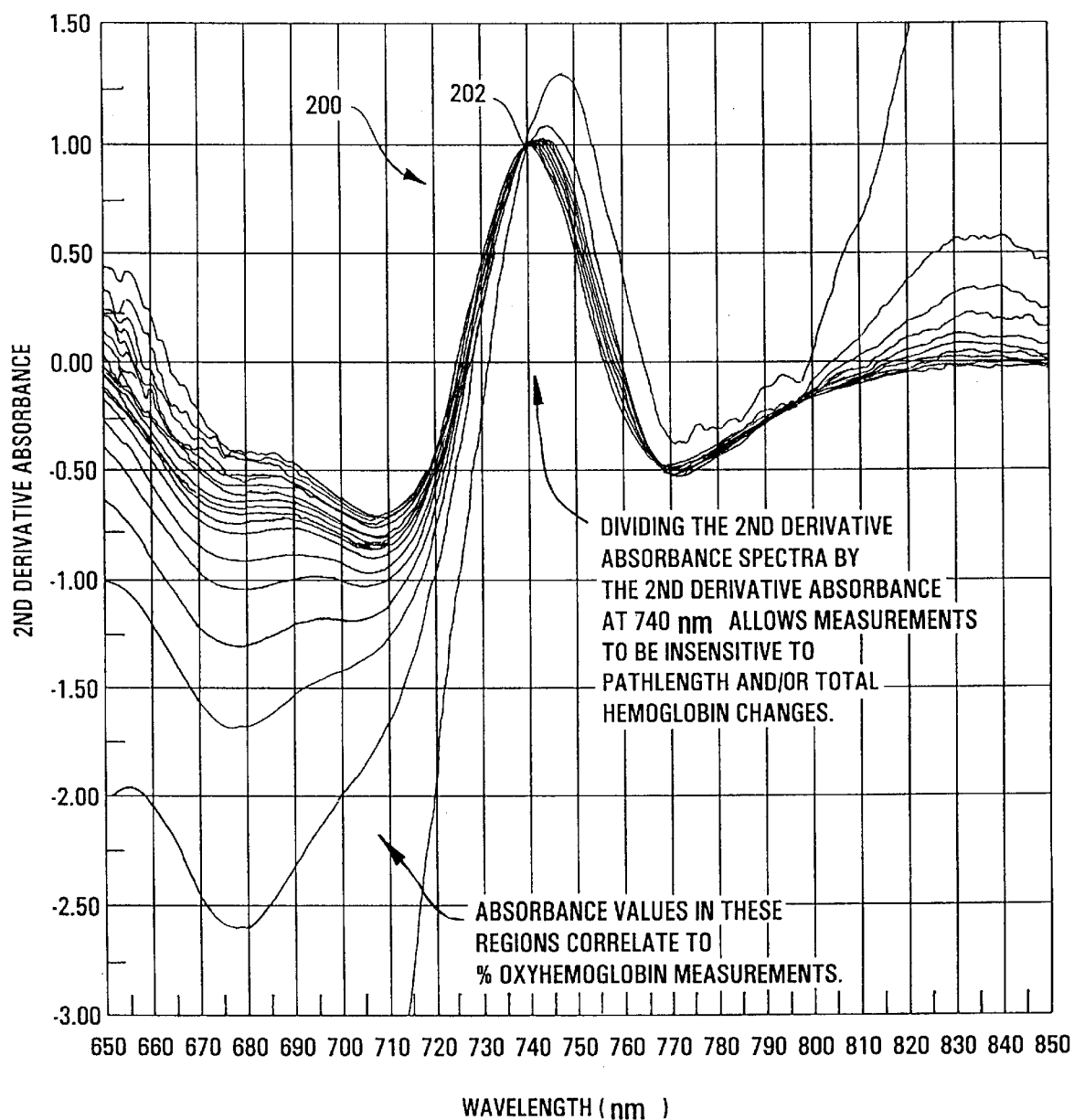
FIG. 3 is a graph which illustrates how proper scaling of a second derivative absorbance spectra makes the second derivative absorbance spectra insensitive (robust) to pathlength and/or total changes in chromophore concentration.

Turning now to FIG. 3, a family of spectral data 200 which is robust to changes in total concentration of hemoglobin and/or optical pathlength is illustrated. It can be seen the family of spectral data 200 retains the spectral characteristics for the measured chromophore as depicted in FIGS. 1 and 2 described hereinbefore. In one preferred embodiment for the present inventive method, the family of spectral data 200 is generated by dividing all of the second derivative absorbance spectra values by the second derivative absorbance value measured at a wavelength of 740 nm for each characteristic data value within the family of spectral data 200. In this manner, the family of spectral data 200 is normalized (scaled) to a value of one (shown by reference number 202) at the 740 nm wavelength. This scaling results in a consistent pattern of data which is substantially unaffected by the optical pathlength and/or total hemoglobin concentration discussed herein above. Looking again at FIG. 3, it can be seen that spectral characteristics further removed from either side of the 740 nm wavelength point show markedly distinct changes in spectral data values. Data values about a wavelength of 680 nm exhibit characteristics especially useful in determining the relative concentrations of oxyhemoglobin with respect to the total concentration of hemoglobin within the blood-containing tissue of interest. In particular, the slope associated with any single characteristic spectrum within the family of spectral data 200 is substantially identical with the slope associated with any other single characteristic spectrum within the family of spectral data 200 when in close proximity to the wavelength of 680 nm, although the actual data values for any single characteristic spectrum within the family of spectral data 200 are dependent upon the actual relative concentration of oxyhemoglobin with respect to the total concentration of hemoglobin. The tissue is irradiated with a broad bandwidth continuous wave spectrum of light to determine a complete spectrum within a spectral region of interest such as any of the single spectrums shown within those families of characteristic curves 10, 100, 200 illustrated in FIGS. 1–3. Alternatively, the present invention can simultaneously irradiate the tissue with a plurality of signals at predetermined, but different wavelengths to determine a sufficient spectrum within a spectral region of interest to generate a family of characteristic spectral data such as illustrated in FIGS. 1–3. Preferably, absorbance values determined from the single spectrum at or about a wavelength of 680 nm can then be correlated to percentage oxyhemoglobin measurements relative to the total concentration of hemoglobin within the tissue. The present invention is not so limited however, and it shall be understood that the present invention can be practiced by irradiating the tissue at a minimum of four distinct and predetermined wavelengths selected to generate spectral data for accurately determining relative concentrations of a first tissue chromophore with respect to a second tissue chromophore.

Figure 4:
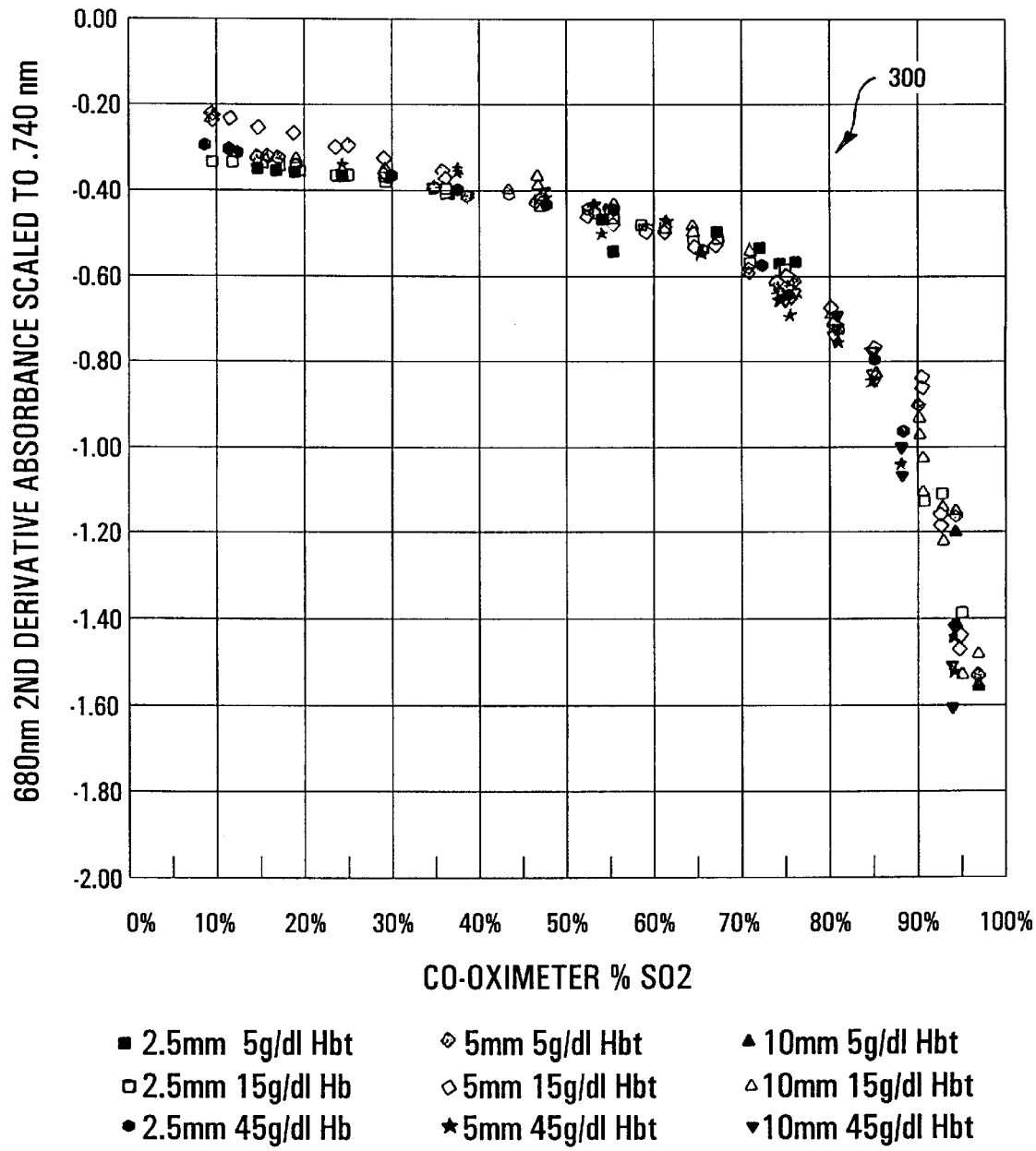
FIG. 4 is a graph which illustrates various calibration curves established for differing relative concentrations of a predetermined chromophore and/or differing optical pathlength conditions, over a spectral region of interest.

Turning to FIG. 4, various calibration curves 300 established for several relative concentrations of the $HbO_2$ chromophore, several total concentrations of hemoglobin ($Hb_t$), and several probe designs (optical pathlength variations) are illustrated. The calibration curves 300 were determined in vitro with blood circuit (shown as 1900 in FIG. 19) measurements and subsequently verified by correlating the in vitro data with data measured in vivo using co-oximeters and actual blood tissue. For the sake of clarity, the methods and apparatus utilized to determine the calibration curves 300 will be discussed in detail later.

Most preferably, calibration data 300 is transferred from the desired calibration curve illustrated in FIG. 4 to a neural network (shown as 2210 in FIG. 22), where additional data correlation, smoothing, filtering and weighting of specific data takes place, prior to generating a quantified output signal representative of a relative concentration of oxyhemoglobin with respect to the total concentration of hemoglobin. Looking again at, and with reference to FIGS. 1–4, one present inventive method for quantifying the relative concentration of oxyhemoglobin in blood-containing tissue can be summarized as follows:

(1) irradiate a predetermined blood-containing tissue with a continuous wave light source having a broad bandwidth, or alternatively, irradiating the tissue at a minimum of four distinct and predetermined wavelengths; (2) measure light emitted from said blood-containing tissue at a plurality of selected discrete wavelengths, sufficient in number to determine and accurately characterize a desired absorbance spectrum within a spectral region of interest having boundaries defined by the aforesaid bandwidth, or alternatively by the four distinct and predetermined wavelengths; (3) transform the absorbance spectrum into a second derivative spectrum; (4) scale the second derivative spectrum such that the spectral value at a first predetermined wavelength, i.e. 740 nm, is normalized to a value of one; (5) using the scaled second derivative absorbance spectrum, determine the spectral nominal amplitude value at a desired and second predetermined wavelength, i.e. 680 nm; and (6) processing the spectral nominal amplitude value at the desired wavelength, i.e. 680 nm, through a neural network, or alternatively using a multiple regression analysis to generate the actual concentration of oxyhemoglobin with respect to the total hemoglobin within the blood-containing tissue.

Figure 5:
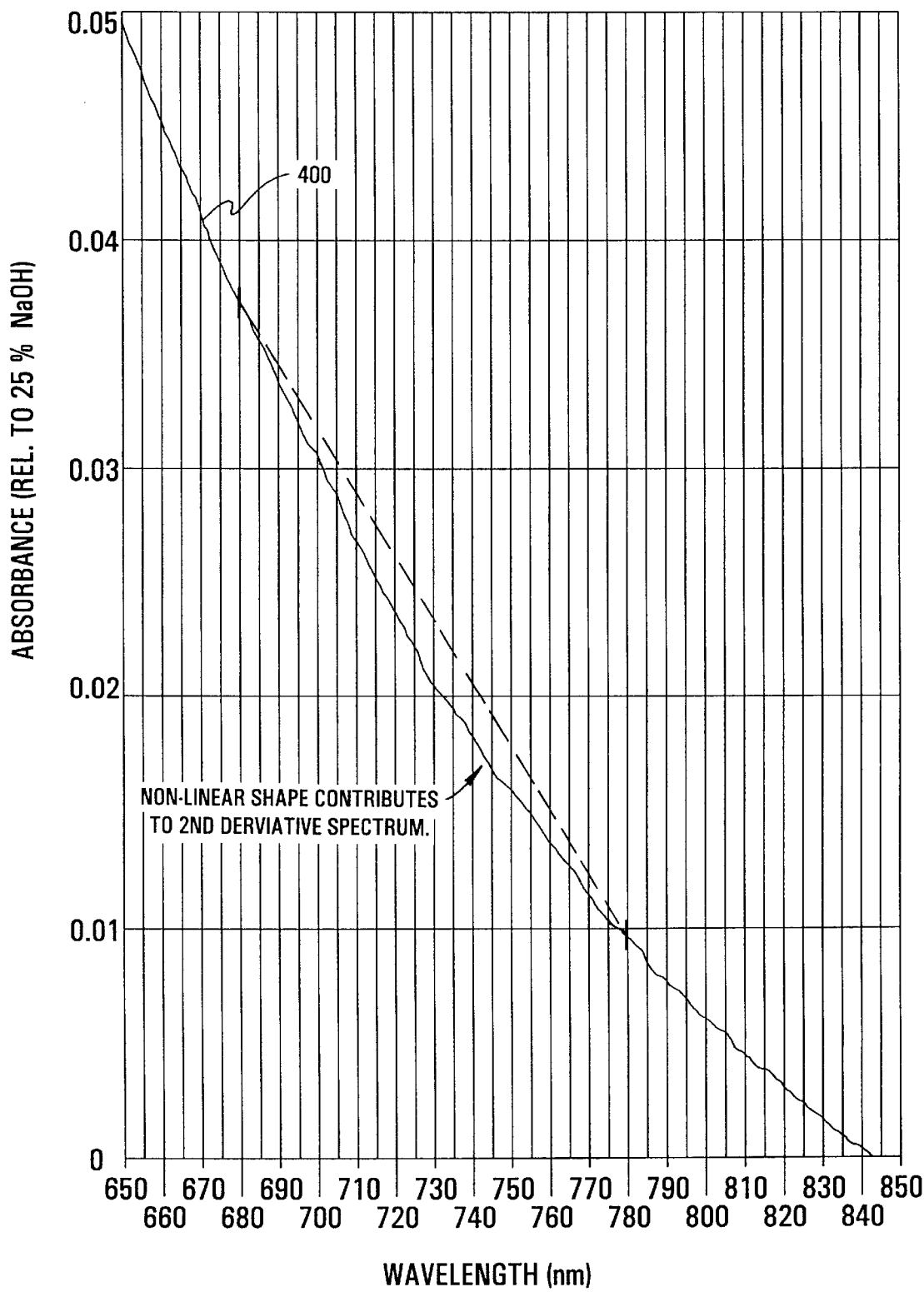
FIG. 5 is a graph which illustrates the nonlinearity of scattering losses and/or interfering spectral contributors (i.e. melanin and bilirubin) which contribute to measurement errors of the predetermined chromophore(s)

Turning to FIG. 5, there is illustrated absorbance spectral data 400 over a continuous broad spectral region (650 nm–850 nm) for melanin. It can be seen that the absorbance spectrum 400 displays nonlinear characteristics at or about a wavelength of 740 nm, which is the wavelength at which one preferred embodiment for the present inventive method normalizes the second derivative absorbance spectrum for the measured chromophore as demonstrated in FIG. 3. That being the case, it is desirable to eliminate the nonlinear effects that melanin contributes to the second derivative absorbance spectral data for the measured chromophore, if melanin exists in the tissue sample. It is believed that the aforementioned nonlinear effects due to the presence of melanin or other interfering spectral contributors including bilirubin, for example, can be eliminated by using a nonlinear transformation such as that depicted in FIG. 6. FIG. 6 demonstrates the results of applying a suitable nonlinear transformation (i.e. $1/wavelength^3$) at each wavelength within the spectral region of interest. The resultant absorbance spectrum 500 now exhibits a shape that is linearized over the desired spectral region, thereby no longer contributing to the second derivative absorbance spectrum for the measured chromophore. In this manner, the accuracy of measurements provided by the present inventive system and method is further optimized.

The foregoing inventive method of measuring relative concentrations of a chromophore such as oxyhemoglobin can be achieved via a measurement system including apparatus described hereinafter in detail with reference to FIGS. 7–24.

Turning now to FIG. 7, a simplified pictorial of a reference canister 600 suitable for calibrating a light detector probe 602 for use with the present inventive system, is illustrated. A measurement of the light source (reference spectrum) as it exits the fiber optic probe 602 is used in the course of transforming a tissue attenuation spectrum into an absorbance spectrum. Comparison of the light source reference spectrum to the spectrum of light received back from the tissue allows an absolute determination of the tissue spectral characteristics. It is believed, without an accurate reference measurement, meaningful quantification of the tissue chromophores of interest would not be feasible. In order to measure a reference spectrum, the fiber optic probe 602 is placed on a reference canister 600 which reflects the send light from optical fibers 604 back through the receive fiber optics 605 to the detector. The reference canister 600 is designed in a manner which allows measurement of the light source spectrum with minimal distortion and/or adding bias to its spectral shape. Most preferably, the reference canister 600 is coated or covered internally over the inner surfaces with a spectrally flat material 606 such as Spectralon® which is commercially available form Labsphere, Inc. of North Sutton, N.H., thereby ensuring that all wavelengths of light emitted from the probe 602 into canister 600 are equally reflected back to the detector probe 600. It is believed that Spectralon®, though it may be a relatively uniform reflector of a broad band of wavelengths, is not a perfect Lambertian scatterer. This means that incident wavelengths will be scattered in slightly different directions. Couple this effect with the numerical aperture of the optic fibers 604, 605, and the closer probe/Spectralon® distances may not allow all the wavelengths to equally enter the receive probe 602 fibers 605 whereas the more distant position does. The change made then to capturing the reference spectra is to hold the distance substantially constant at preferably a minimum of 25 mm above the Spectralon® surface. Preferably, detector probe 602 includes optical fibers 604 suitable for transmitting broad bandwidth light from a broad bandwidth light source such as a tungsten-halogen lamp, shown as 1402 in FIG. 14, and also optical fibers 605 suitable for detecting broad bandwidth light emitted from a tissue which could be a blood-containing tissue or a tissue not perfused with blood that contains the chromophore to be examined. The canister 600 itself can be constructed of any suitable material such as a plastic or a metal, for example, so long as the functionality of the canister 600 is maintained with respect to the detector probe 602.

A high pass filter 1406, i.e. 500 nm, can be included within the light path preferably within the light source assembly (shown as 1406 in FIG. 14) to eliminate second order diffracted light at wavelengths below 500 nm. Below 500 nm, a small amount of the original input light will be generated within a spectrometer at wavelengths twice the incoming, i.e. there is a fraction of 400 nm light appearing as 800 nm light. Since the high pass filter 1406 blocks the lower wavelengths, there is relatively little concern of this occurring.

FIG. 8 illustrates in greater detail one preferred embodiment of the reference canister 600. Preferably canister 600 is designed to have an opening 700 that is adapted to tightly mate with the detector probe 602 such that broad bandwidth light emitted from and/or detected by optical fibers 604, 605 exclude ambient light and is equally reflected off the internal surface areas of the canister 600, as stated hereinbefore. Although a particular embodiment for the canister 600 is illustrated in FIG. 8, it will readily be appreciated that many other embodiments for the canister 600 will also function with the present inventive system, so long as the reflectance characteristics are maintained within the alternative embodiment.

Figure 9:
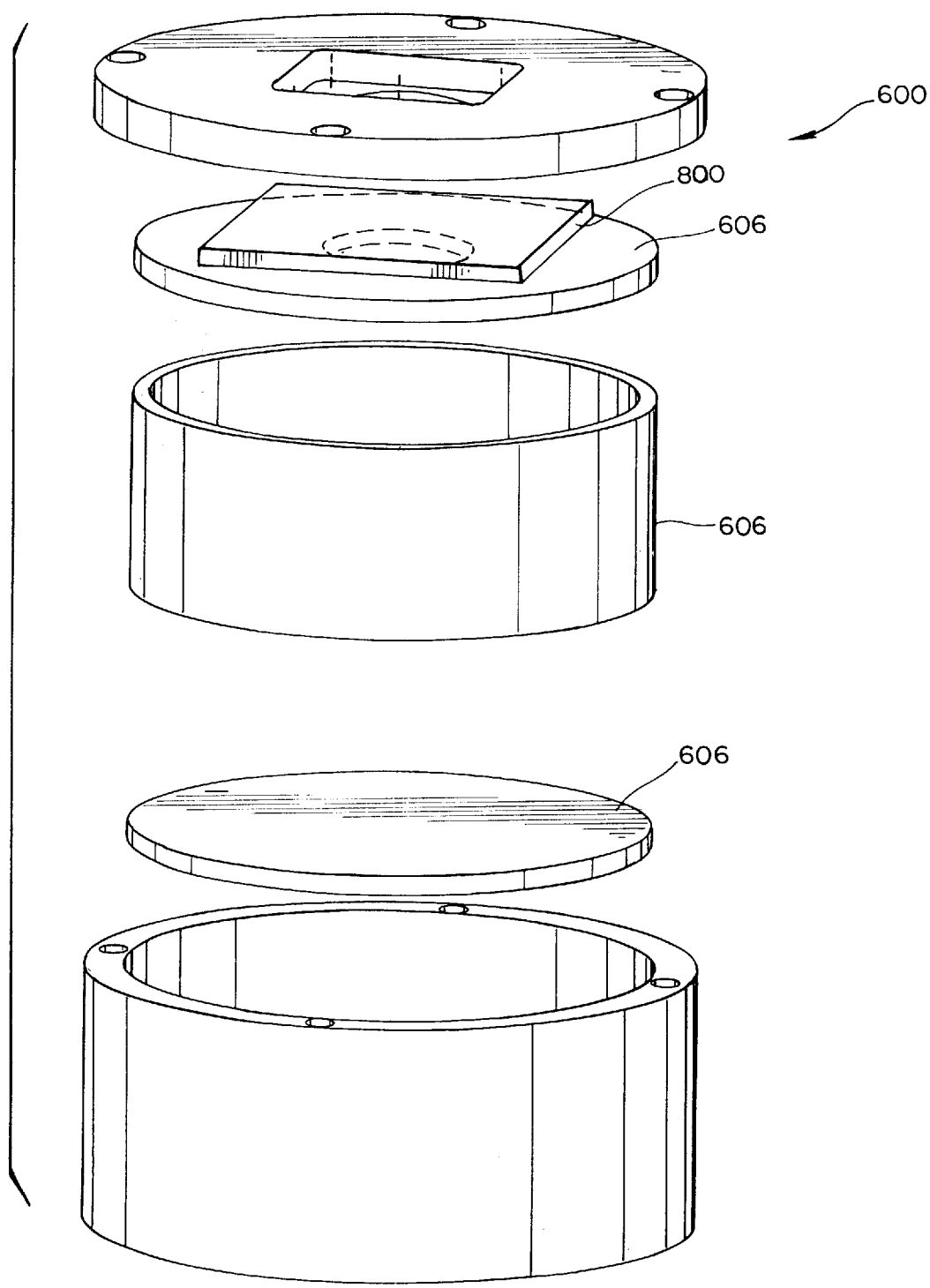
FIG. 9 illustrates a detailed view of the preferred embodiment for the reference canister depicted in FIG. 7.

FIG. 9 illustrates a more detailed view of the preferred embodiment for the calibration canister 600 shown in FIG. 8. The preferred embodiment contains an internal multi-bandpass glass filter 800 which produces a series of transmission peaks. The filter 800 used in one preferred embodiment is made of Didymium, and is a model BG-36 manufactured by Schott Glass Technologies, Inc. of Duryea, Penn. Light transmitted through the filter 800 and back through the detector probe 602 will induce spectral peaks at known wavelengths which can be used to calibrate the detector probe 602. Tests of the filter 800 have shown that the wavelength peaks do not shift as the temperature is fluctuated from 21° C.,+/−5.6° C. The probe 602 calibration method includes an examination of a standard spectral peak, i.e. 551 nm, 708 nm, 774 nm and 843 nm, and if found to have shifted from its true values due to misorientation between the probe 602 and the detector, for example, the detector calibration coefficients are adjusted automatically with a software peak finding routine. Such peak finding routines are well known to those skilled in the art of signal filtering and digital signal processing, and so will not be discussed herein for the sake of clarity and brevity. It will readily be apparent to those skilled in the art that any standard spectral peak residing at or near the wavelengths of interest will be useful in calibrating a detector probe of similar design and functionality as that described herein. Additionally, it will be readily apparent that any other non-flourescing material exhibiting substantially the same reflective characteristics as Didymium will also work in the present inventive calibration apparatus to establish a baseline reflectance spectrum for the present inventive system.

Turning to FIGS. 10a–10d, and specifically to FIGS. 10a and 10b, one preferred embodiment 900 is shown in FIG. 10b which illustrates a pattern of optical fibers 604, 605 coupled to a probe 602 to establish an absorbance spectrum, such as those depicted in FIGS. 1–3, suitable for use with the present invention. It is readily apparent to those skilled in the art of fiber optics, that greater optical penetration within a particular tissue may be achieved by the addition of more optical fibers 604 to the light probe 900 to increase the intensity of light emitted from the optical fibers 604 utilized to transmit the light 902 emitted by the light source, coupled with, increasing the spacing between the send optical fibers 604 and the receive optical fiber 605, thereby giving greater depth of radiation penetration prior to detection of light emitted from the tissue. FIG. 10d illustrates another preferred embodiment 1000 for a pattern of optical fibers 604, 605 coupled to a probe 602 to establish an absorbance spectrum, such as those depicted in FIGS. 1–3, and suitable for use with the present invention.

Figure 11:
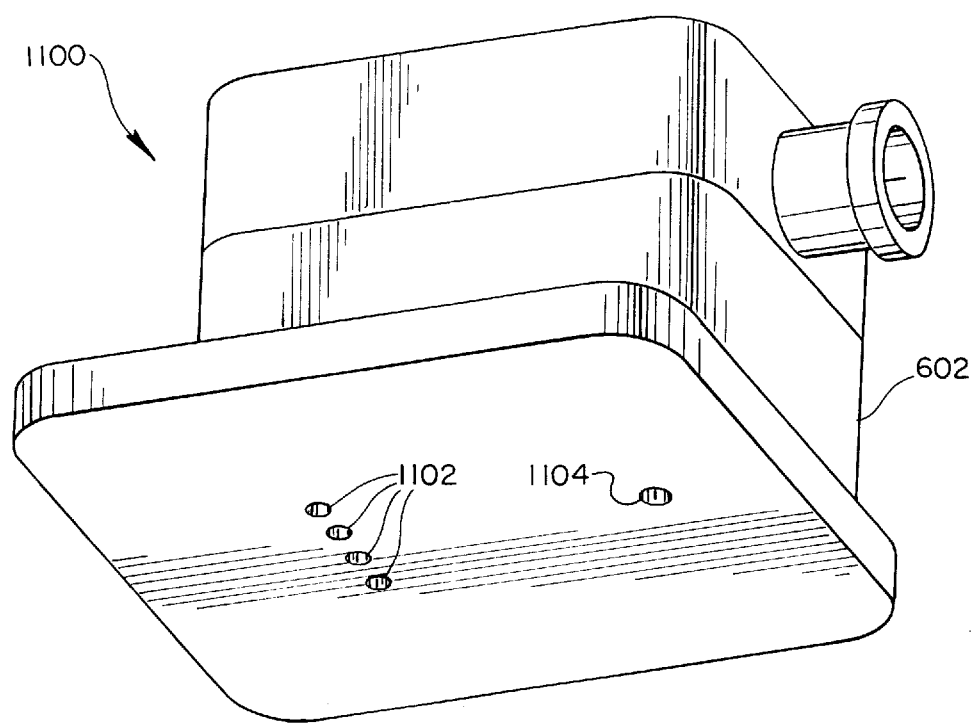
FIG. 11 illustrates one preferred embodiment for a light probe suitable for use as a interface between the send/receive fibers and the measurement media.

Turning now to FIG. 11, one preferred embodiment for a fiber optic probe 1100 suitable for use with the present inventive system is illustrated. Transmission optic fibers 604, attached to the probe 1100 at points designated as 1102, are used to transmit light from a light source to the surface of a predetermined tissue of interest; and a receive optic fiber 605, attached to the probe 1100 at the point designated as 1104, is used to receive light emitted from the tissue. It can be seen the transmission optical fibers 604 are coupled to the body 602 of the probe 1100 in a linear pattern at attachment points 1102 as contrasted to the circular pattern illustrated in FIG. 10b and the single point pattern illustrated in FIG. 10d. It is believed that the particular pattern of optic fibers 604, 605 selected for use is not critical to practicing the present inventive method, so long as the specific probe used to irradiate the tissue of interest, has been properly calibrated, using calibration methods described in detail herein.

Figure 12:
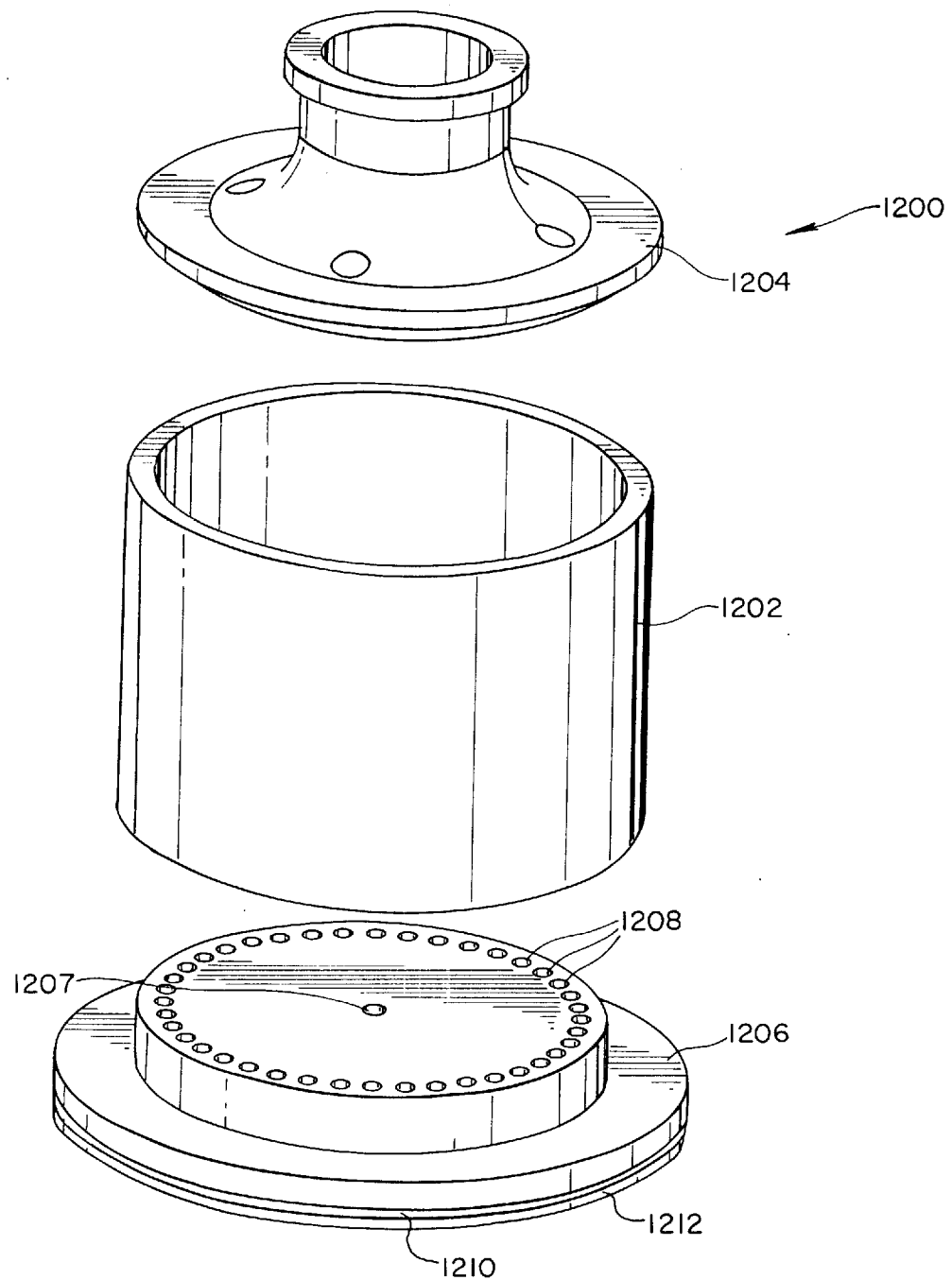
FIG. 12 illustrates yet another preferred embodiment for a light probe suitable for use as a interface between the send/receive fibers and the measurement media.
Figure 13:
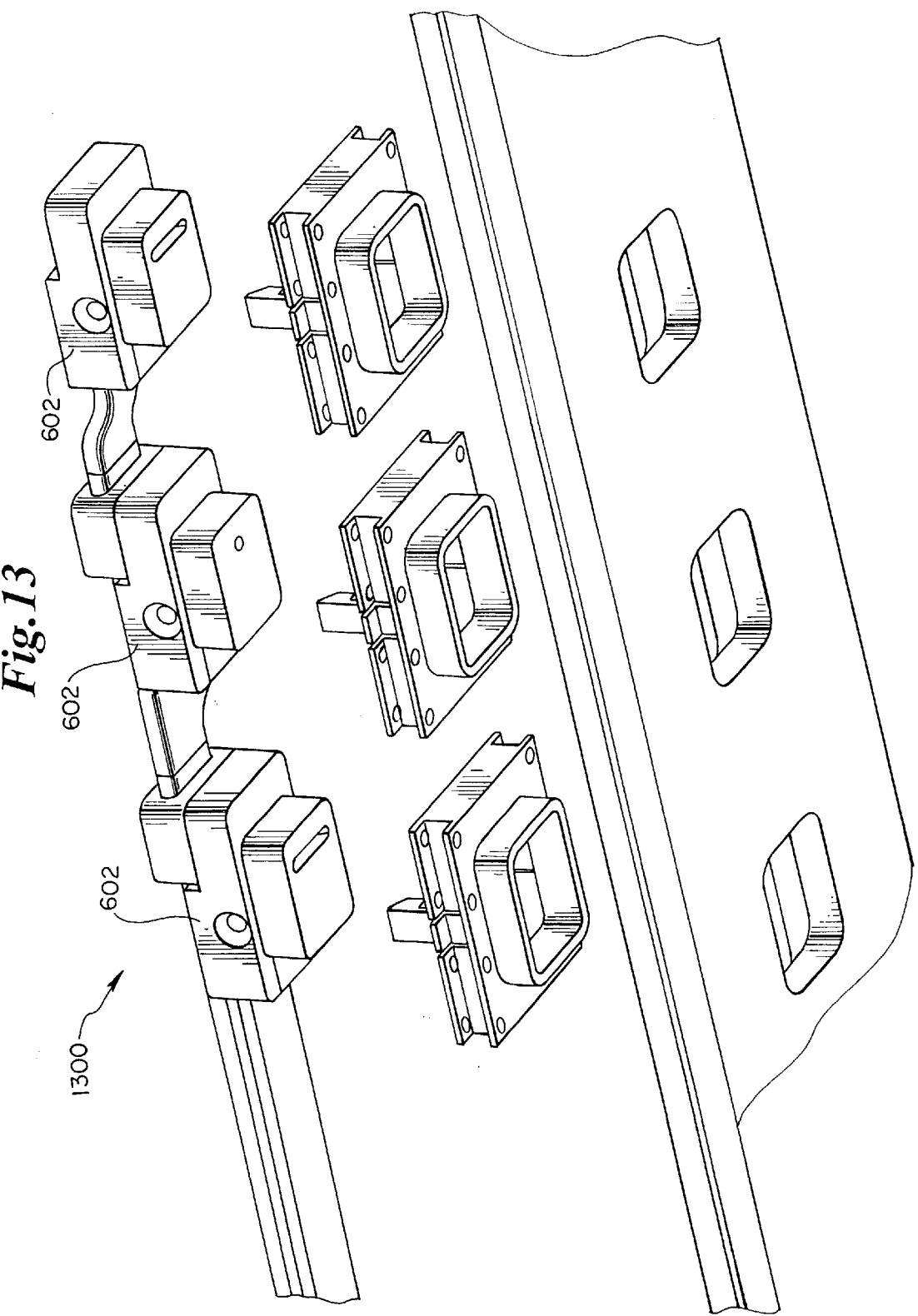
FIG. 13 illustrates one preferred embodiment for a multi-piece light probe suitable for use as a interface between the send/receive fibers and the measurement media.

FIG. 12 illustrates yet another embodiment for a fiber optic probe 1200 which is suitable to practice the present inventive method. The probe face 1206 has been adapted to accept a very large number of optic fibers 604, 605 to increase the intensity of light transmitted to the surface of the tissue. Transmission optical fibers 604 are attached to the probe face 1206 in a circular pattern at attachment points designated as 1208 in FIG. 12. The receive fiber 605 is attached to the center of probe face 1206 at point 1207. It is readily seen that the probe 1200 need not be formulated as a single piece, but may be a combination of parts 1202, 1204, 1206, 1210, 1212 as depicted in FIG. 12. Furthermore, the present inventive method and system is not limited to use of a single probe 602, 1100, 1200. Several probes 602, 1100, 1200 could be used simultaneously to achieve the desired results. For example, it was found preferable by the present inventors to have at least one multi-probe embodiment, shown as 1300 in FIG. 13, capable of individually or simultaneously obtaining shallow and/or deep signal measurements for the tissue being irradiated. Alternatively, the multi-probe embodiment 1300 depicted in FIG. 13, offers added flexibility in that individual probes 602, 1100, 1200 may be removed or added to the multi-probe configuration 1300, as desired.

Generally, the purpose of the probe 602, 1100, 1200 is to act as the interface between the send/receive fibers 604, 605 and the measurement media, i.e. tissue. The probe 602, 1100, 1200 may house the send/receive fibers 604, 605 in different configurations ranging from linear to circular with respect to each other, as described herein above in detail. Furthermore, the use of multiple receive optical fibers 605 to transmit light to the input of an array (shown as 1504 in FIG. 15) results in substantial reduction in time variant interferometric noise in received spectra. Because of crosstalk concerns, it is believed that constructing probe 602, 1100, 1200 of an opaque, nonfluorescing material will prevent light from the send fibers 604 seeping into the receive fibers 605. It is also important that the probe 602, 1100, 1200 be made of a material, such as Radel® R5500 polyphenylsulfone, commercially available from Amoco Performance Products, Inc. ("APP") of Marietta, Ohio, that is spectrally flat in the wavelength region of interest. This is because a portion of the light that hits the underside of the probe 602, 1100, 1200 as it tries to leave the tissue (i.e. skin) is reflected back into the tissue, some of which may make its way back into the receive fibers 605. The same rationale holds true for the reference canister 600. It is important that this spectra of reflected light is not significantly changed due to its interaction with the probe material. The send/receive fibers 604, 605 as they are housed in the probe 602, 1100, 1200 may be at an angle with respect to each other. The fibers 604, 605 themselves may come into the probe 602, 1100, 1200 at various angles as well, e.g. 90° or straight in or something in between, such as illustrated in FIG.'s. 17*f*, 17*g*, 17*h* and 17*i*.

Depending upon the volume of tissue that is desired to be sampled, the probe 602, 1100, 1200 must be designed and manufactured with appropriate distances between the send fibers 604 and receive fibers 605. The depth of the tissue sampled may also be controlled to a certain extent by changing the reflection properties of the underside of the probe 602, 1100, 1200 in the area between the send fibers 604 and receive fibers 605. Materials (i.e. white Delrin® commercially available from E. I. DuPont De Nemours & Co., of Wilmington, Del. or Teflon®, also commercially available from E. I. DuPont) that reflect light amplify shallow depth measurements since light exiting the tissue underneath the probe 602, 1100, 1200 surface is continually reflected back into the tissue. This re-reflected light has a send/receive distance that is smaller than the primary send/receive distance and therefore takes a shorter optical path within the tissue.

Materials, e.g., black Radel® from APP or Neoprene® (faced with antimicrobial black nylon fabric) which are commercially available from Rubatex Corporation of Bedford, Va., that absorb light do not exhibit shallow depth amplification.

Looking again at FIG. 12, probe 1200 can optionally have an IR cutoff filter 1210 attached to the face of the probe 1200 that comes into contact with tissue. The IR cutoff filter 1210 reflects IR radiation back to the light source (shown as 1400 in FIG. 14). This results in reduced tissue heating, reduced temperature rise in the IR filter 1210, lower intensity at the tissue due to increased distance between fiber 604, 605 tips and tissue, and minimization of localized tissue heating due to heat spreading effects of the filter 1210. Generally, the use of any transparent glass filter over the face of the tissue probe 1200 minimizes tissue heating through increased fiber 604, 605 to tissue spacing and heat spreading effects.

Probe 1200 can also be adapted to interface with tissue by application of a substantially transparent disposable tissue dressing 1212 over the probe 1200 face to minimize probe 1200 contamination with minimal spectral influence. Tegaderm, commercially available from 3M Co. of St. Paul, Minn., was found to have minimal attenuation and to exhibit spectrally flat second derivative absorbance characteristics in the wavelength region of interest.

Figure 14:
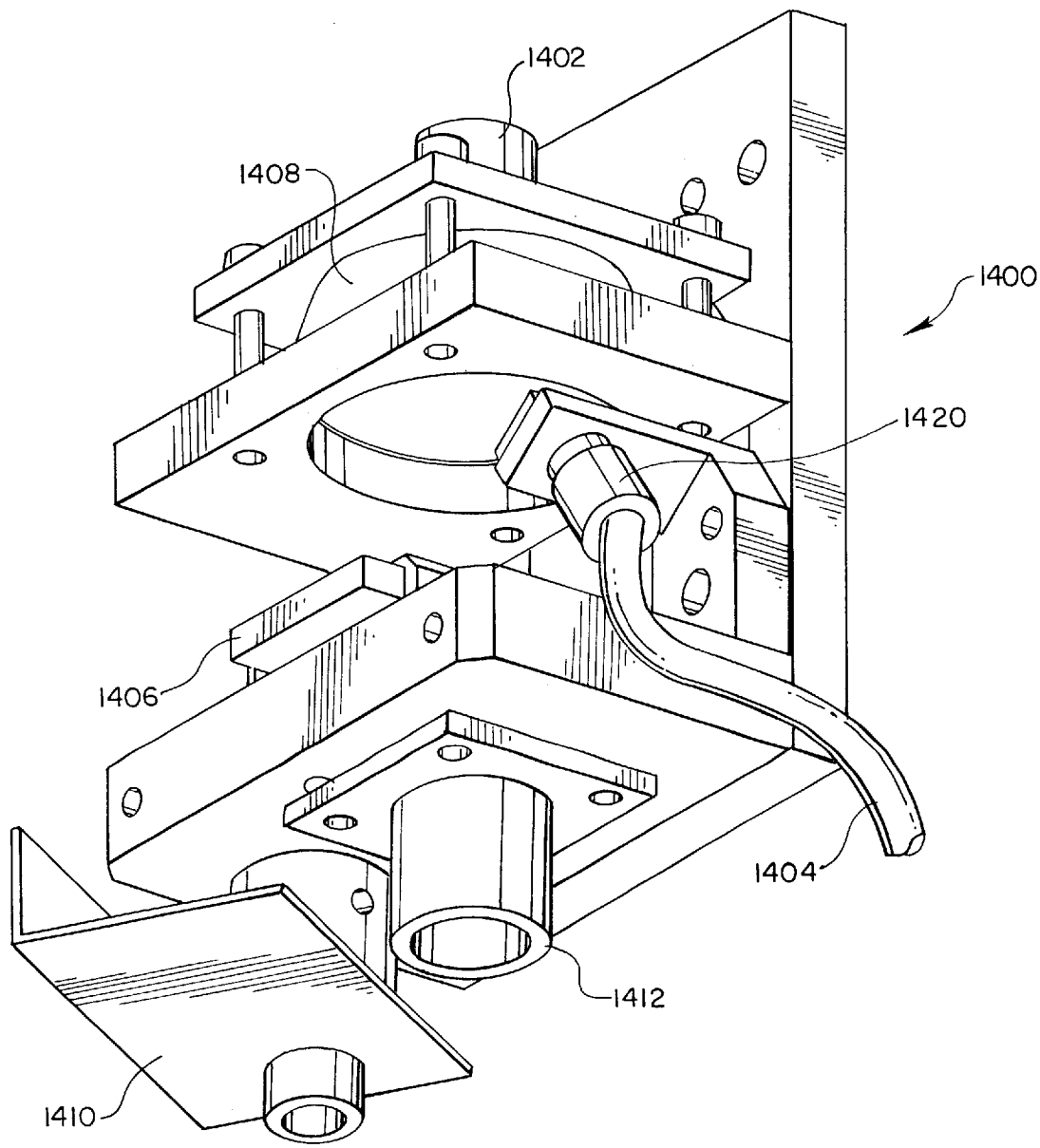
FIG. 14 illustrates one preferred embodiment for a light source assembly suitable for use with the present inventive measurement system to provide illumination through the optical send fibers.

Turning to FIG. 14, there is illustrated one preferred embodiment for a light source assembly 1400, suitable for use with the present inventive system. A broad bandwidth lamp 1402 provides the source of illumination for the light transmitted through the transmission optic fibers 604 (not shown in FIG. 14). Tungsten-Halogen bulbs which are commercially available from Welch Ally of Skaneateles Falls, N.Y., and are commonly used in NIR Spectrometry are suitable for use as the lamp 1402. Limitations in warm-up time, amplitude stability, color temperature changes, and time dependent changes in filament image all contribute to measurement errors. To compensate, many systems make a reference spectral measurement prior to each sample measurement.

Figure 15:
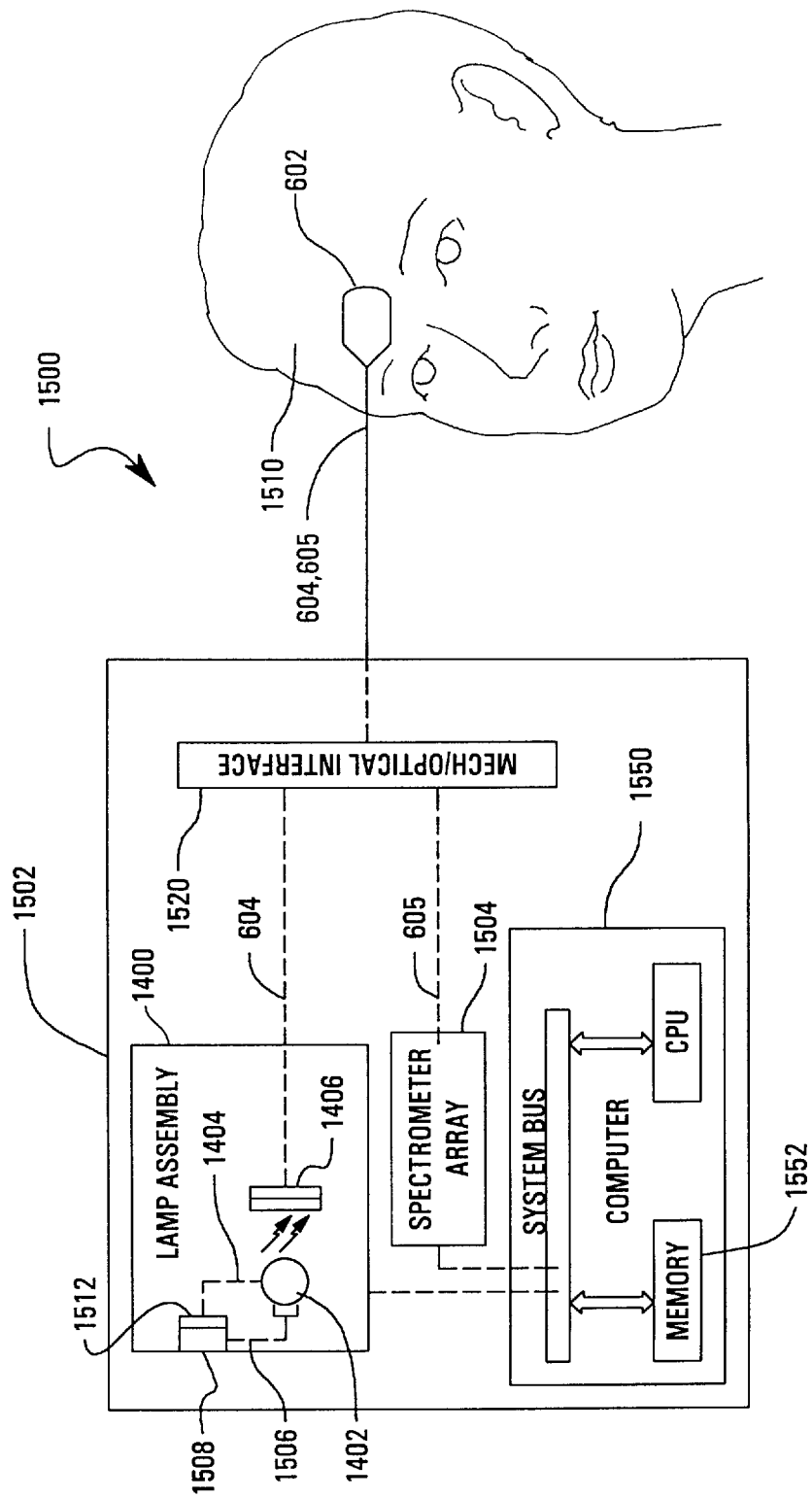
FIG. 15 illustrates a monitoring console having an array spectrometer for detecting light emitted from a predetermined blood-containing tissue.

Light source assembly 1400 utilizes optical fibers 1404 which are aimed at the lamp 1402 and transmit light emitted by lamp 1402 to an optical power sensor (shown as 1512 in FIG. 15). Such power sensors are well known to those skilled in the art, and will not be discussed herein to preserve clarity and brevity. The output of the power sensor 1512 is maintained constant through feedback adjustment of the lamp 1402 voltage and/or current. Stabilization of the light source assembly 1400 in this manner minimizes signal drift due to lamp 1402 aging and reduces the frequency of reference measurements made necessary. A pulse width modulating controller 1508, shown in FIG. 15, the use of which is well known, is used to adjust the lamp 1402 voltage and/or current based upon the light intensity received from the feedback optical fiber 1404. Lamp 1402 feedback fiber(s) 1404 is arranged to capture a majority of lamp 1402 filament image to provide a signal closely proportional to total lamp 1402 output and thus avoid amplitude drift due to time dependent intensity profile shifts in filament image. The feedback fiber(s) 1404 is optionally arranged in a side firing configuration to sample light at a focal point similar to the focal point of the send (transmit) optical fiber 604 following installation, thereby minimizing errors and feedback signals due to thermal effects on filters 1406 and focus. Optionally, the feedback fiber(s) 1404 is disposed within the transmit optical fiber 604 bundle to provide a signal most representative of that transmitted to the probe 602, 1100, 1200, and robust to any changes in the optical path between filament and connector such as filter thermal effects or connector movement. The feedback signal fiber(s) 1404 is then "pigtailed" back to the power sensor 1512 via a fiber optic connector.

Controller 1508 is designed to operate with a fundamental switching frequency chosen which has a period much less than the thermal time constant of the lamp 1402 to minimize intensity ripple and maximize bulb life without use of cumbersome and costly LC output filters. Pulse width modulation control enhances the lamp 1402 and controller 1508 power efficiencies resulting in reduced heat generation within the embodied signal detector monitor console (shown as 1502 in FIG. 15) incorporating the lamp assembly 1400, illustrated in FIG. 15.

Figure 23:
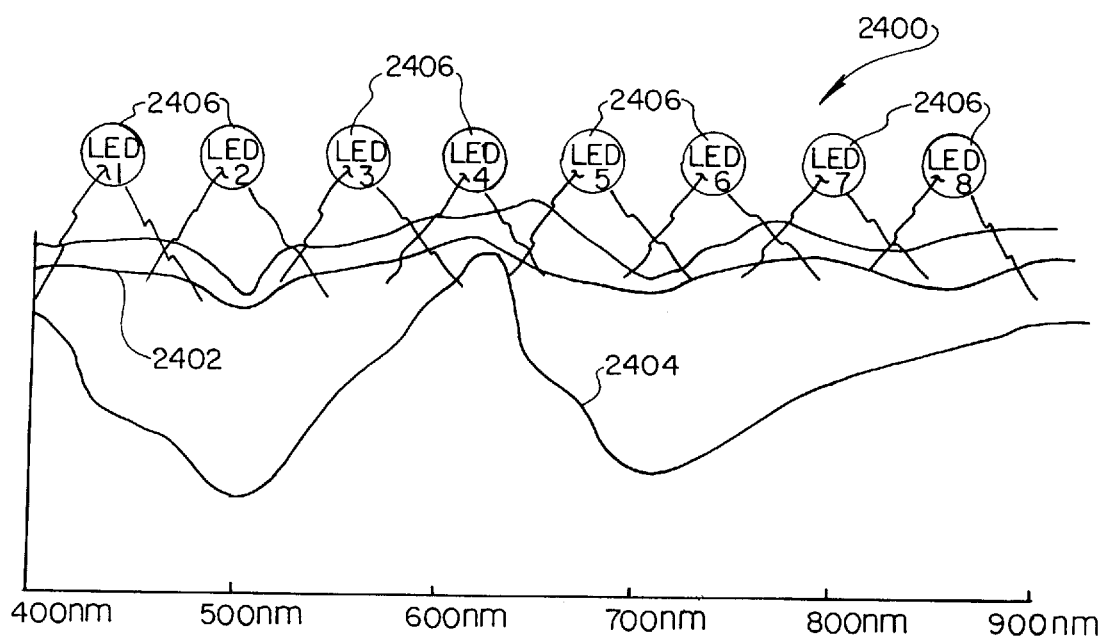
FIG. 23 illustrates a plurality of narrow bandwidth light sources which are combined to emit a spectrum of light having a wide bandwidth.

It shall be understood that the present invention is not so limited to the embodiment shown in FIG. 15, however, and that many other configurations and combinations of light sources and monitor consoles may also function equally well in practicing the present inventive method. For example, it is possible to create a light spectrum having a broad bandwidth by combining the light spectrums created by a plurality of narrow bandwidth light sources having overlapping light spectrums to effectively eliminate any gaps or discontinuities within the resultant spectrum of light generated when combining the aforementioned narrow bandwidth spectrums of light. FIG. 23 illustrates one such combination of light sources 2400 in which a group of narrow bandwidth light emitting diodes (LEDs) 2406 are combined to generate a spectrum of light which covers the spectral region between 400 nm and approximately 900 nm. The broad bandwidth spectrum of light generated by the LEDs is sufficient to measure chromophores which exhibit characteristic depicted by the specific spectral data 2402 and 2404, for example, without leaving any spectral gaps.

As stated hereinbefore, the present invention may also be practiced without the aid of a continuous wave broad bandwidth light source. The methodology could incorporate the use of four or more narrow bandwidth light sources such as LEDs 2406, selected to have radiation wavelengths sufficient to enable construction of predictive mathematical models necessary to quantify relative concentrations of specific chromophores. Thus, it is not necessary that a combination of light emitting diodes 2406 generate a broad bandwidth spectrum of light to practice the present invention, so long as the appropriate data can be extracted to determine the necessary predictive mathematical models at the aforesaid four or more radiation wavelengths.

Looking again at FIG. 15, the monitor console 1502 can be seen to include a spectrometer array 1504. In order to maintain the spectrometer array 1504 at a fixed low temperature, i.e. 25 deg C., minimal heating within the monitor console 1502 is desired. To further optimize the feedback control of the lamp 1402 intensity within a specific wavelength region of interest, at least one bandpass filter (i.e., IR filter in combination with a high pass filter) 1406 that truncates light signals from wavelength regions of non-interest may be incorporated within the feedback optical path 1506. The bandpass filter 1406 minimizes response to out of band wavelengths, thus providing enhanced control stability for signals at wavelengths of interest.

The spectrometer array 1504 (detector) receives the light signal which is attenuated within the tissue and transmitted through the receive optical fibers 605. The attenuated tissue wavelength spectrum is compared to the reference spectrum (light not attenuated by tissue, as stated hereinbefore), to facilitate tissue absorption measurements at specific wavelength regions.

Detection of signals at multiple wavelengths is simplified with the use of an array spectrometer 1504. Detection is simultaneous and a broadband light source 1400 may be used. There is no practical limit on the number of signals at distinct wavelengths that can be detected within the spectral range of the light source 1400 and array 1504. The array spectrometer 1400 is designed around optic fiber 604, 1404 coupling.

If a linear array spectrometer is used, two types of arrays can be incorporated: charge coupled device (CCD) coupled silicon (Si) photodiode arrays (diode array), and CCD metal oxide silicon (MOS) capacitor arrays. The major benefit derived from using capacitor arrays rather than diode arrays is in small signal extraction due to their much lower noise levels. The primary trade-off in using capacitor arrays is their limited spectral response as compared to diode arrays. For example, the sensitivity peak of the NEC capacitor array currently used in the OCEAN OPTICS spectrometer has been estimated to be 550 nm with a roll-off to 10% at 900 nm. Capacitor arrays are available with a spectral response that peaks at a longer wavelength. A good example is the EG&G RETICON RL 1024J commercially available from EG&G Reticon of Salem, Mass., which peaks at 825 nm and rolls off to 50% at 550 nm and 900 nm, for example. By comparison, a RETICON SC series diode array, designed for spectrometry, peaks at 750 nm and rolls off to 75% at 600 nm and 900 nm. One preferred embodiment of the system is implemented using capacitor array technology.

Figure 16C:
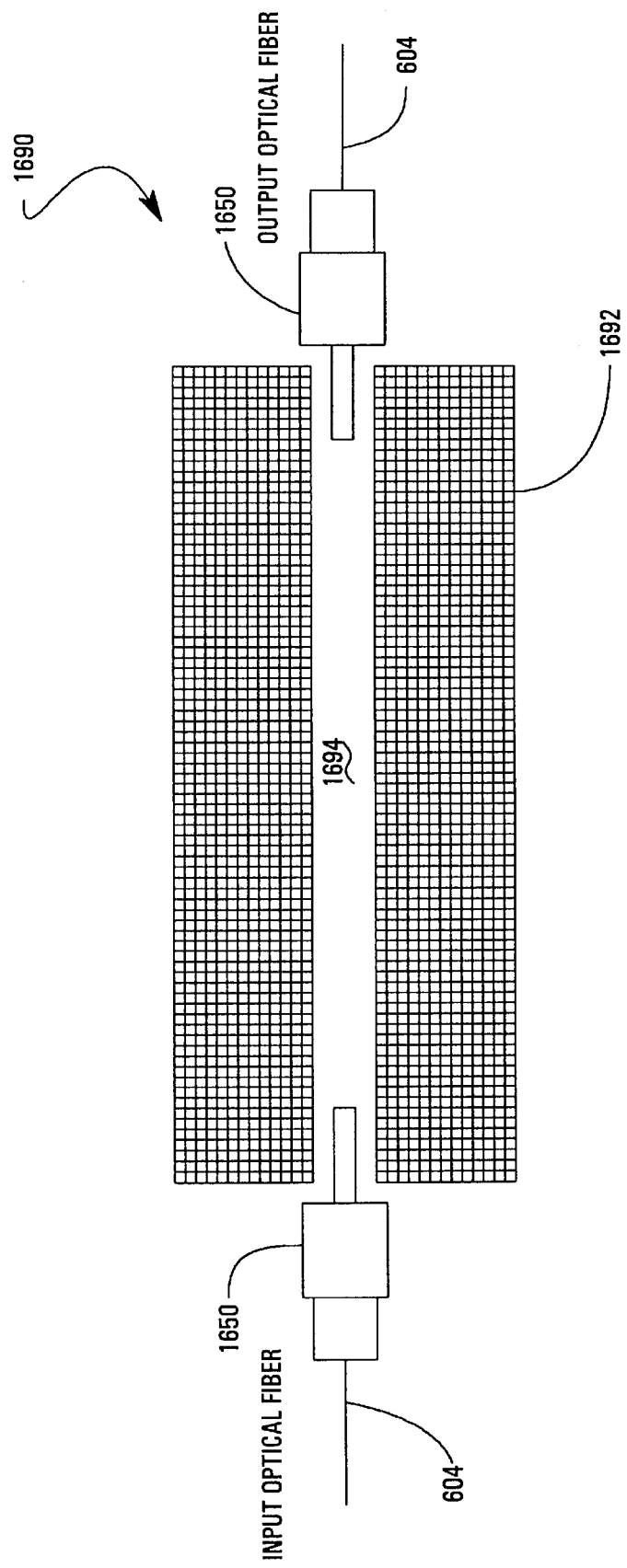
FIG. 16c illustrates one preferred embodiment for a fiber optic coupler and attenuator to match signals from probes with small spacing to the signal level from larger spacing probes while maintaining relative spectral flatness, suitable for use with the present inventive measurement system.

The multiple wavelength signal measurement console 1502 can also be adapted to incorporate use a fiber optic coupler and attenuator such as shown as 1690 in FIG. 16c to accomplish the mechanical/optical interface shown as 1520 in FIG. 15. FIG. 16c illustrates the use of an inline optical attenuator 1690 to match signals from probes of small spacing to the signal level from larger spacing probes while maintaining relative spectral flatness by use of spectrally flat material, i.e. Radel®. The inline optical attenuator 1690 can be used with the monitor console 1502, for example, to couple fiber bundles of different size and number. The connector shown as 1650 in FIG. 16b or any commercially available fiber optic connector, could be used to form the coupler/attenuator assembly 1690. It is important that the length of the attenuator body 1692 be chosen with a sufficient overall length to ensure overlapping of images when coupling multiple fibers. The inherent attenuation characteristics of assembly 1690 will be increased in proportion to length and diameter of the light passage 1694 for passage of light. Attenuation characteristics can also be altered by manipulation of reflectivity of attenuator 1692 body material or by coating the light passage 1694 with a suitable material. Larger values of attenuation can also be established by modifying the light passage 1694 to have a 90° bend in the center, for example. It is believed that fiber optic coupler and attenuator assembly 1690 is a viable alternative to the use of an integrating sphere, offering greater versatility and being more compact.

Returning to FIG. 14, the lamp 1402 is preferably shrouded within an elliptical reflector 1408 which focuses the light to the surface end of the optical fibers 604 which transmit light to the tissue 1510 shown in FIG. 15, for example. Focusing the light emitted by lamp 1402 allows the use of a lower wattage lamp 1402 to achieve sufficient illumination of the tissue 1510. The reduced power requirements of the lamp 1402 minimize heating affects within the monitor console 1502 and increases the life of the lamp 1402. Preferably, a manual shutter 1410 is utilized to protect an operator from exposure to stray light when a probe 602, 1100, 1200 is disconnected from the monitoring console 1502. It is also preferable that lamp 1402 is controlled so that light emitted by lamp 1402 can be turned on and off during periodic measurements of dark current (the spectrometer 1504 response without a light signal) and ambient light correction for calibration purposes described herein.

Lamp assembly 1400 is preferably designed in a manner which fixtures the lamp 1402 in a fixed location with respect to the transmission optic fibers 604 such that the bandpass filter 1406 minimizes transmission IR light energy to the tissue 1510 and cuts off lower wavelength light that would contribute to second order measurement errors within the wavelength region of interest, the most preferred cutoff wavelengths being 900 nm and 500 nm for IR light energy and lower wavelength respectively.

Turning to FIG. 16a, one preferred embodiment is shown for a receive connector plug 1600 which stabilizes the spatial relationship between selected ends of the receive optic fibers 605 and which is suitable for use with the spectrometer array shown as 1504 in FIG. 15. In order to maximize the tissue/detector signal, the barrel tip of the connector plug 1600 is designed to accept the maximum number of receive fibers 605 allowable within the confines of the barrel diameter. The barrel stacks the optical fibers 605 in a slit pattern, shown as 1602 in FIG. 16a, which is perpendicular to the detector optical mounting bench (not illustrated) contained with the monitor console 1502. Since the optical bandwidth is primarily determined by the numerical aperture and diameter of the optical fiber 605, patterning multiple fibers 605 in a slit pattern 1602 maintains an optimal bandwidth which could only otherwise be obtained with only one fiber 605 if the slit arrangement was not used. As stated hereinbefore, the connector plug 1600 is designed to provide repeatable alignment of the optical fiber slit 1602 with respect to the detector optical mounting bench attached to the monitor console 1502. The barrel tip diameter/position and the plug 1600 features are toleranced to allow for interchangeable probes 602, 1100, 1200 between monitor consoles 1502, while minimizing measurement errors due to slit 1602 misalignment and positioning (optical bandwidth and detector 1504 wavelength calibration are maintained). The connector plug 1600 interior design along with a precision manufactured optical mounting bench combine to provide precise parallel and planar positioning of individual optical fibers 605. This leads to signal amplitude and optical bandwidth repeatability between interchangeable probe 602, 1100, 1200 assemblies. Due to the mechanical interaction between the receive connector plug 1600 and its receptacle within the optical mounting bench, the wavelength calibration of the monitor console 1502 is subject to change upon every receive connector plug 1600 insertion. Thus, as stated hereinbefore, a filter 800 is used within the calibration/reference canister 600 that has multiple transmission peaks of known wavelengths. The probe 602, 1100, 1200 is then calibrated after it is connected to the measurement console 1502 by receiving light that has been transmitted through the filter 800. A software routine finds these peaks and assigns calibration coefficients to the spectrometer 1504 contained within the measurement console 1502, thereby achieving the wavelength calibration.

FIG. 16b illustrates one embodiment for a transmit connector plug 1650 which is designed to be coupled to the lamp assembly 1400 within a mating receptacle shown as 1412 in FIG. 14 to stabilize the ends 1652 of the one or more transmit optic fibers 604 with relation to the fixed focal point of the lamp 1402. It was found most preferable to polish the ends 1652 of the transmit optic fibers 604 flush to the plug 1650 surface 1654 which mates with the connector plug receptacle 1412. Specifically, the plug 1650 mates to the receptacle 1412 so that the ends 1652 of the transmit optic fibers 604 are located within the focal area of the elliptical lamp reflector 1408. The plug 1650 maximum bore diameter closely matches the focal point area of the lamp 1402 and thus maximizes the light intensity transferred to the transmit optic fibers 604.

Figure 17G:
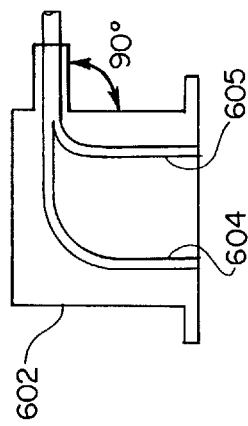
FIGS. 17f–17i illustrate different optical fiber/probe interface configurations are suitable for use with the present measurement system.
Figure 17I:
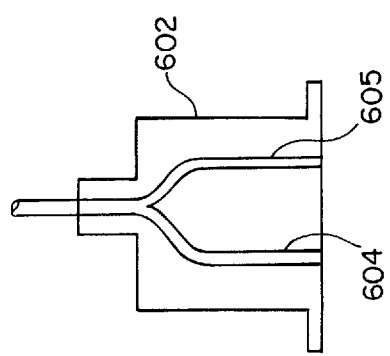
Figure 17F:
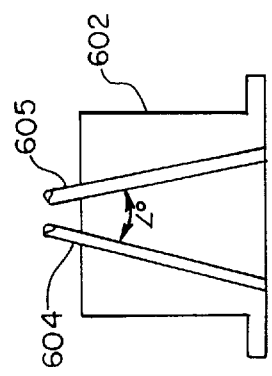
Figure 17H:
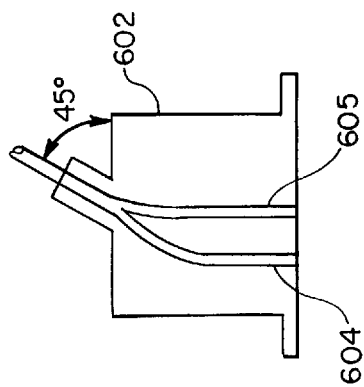

Turning to FIG. 17, and particularly to FIGS. 17a, 17b, 17c, 17d and 17e, different end configurations are illustrated for the optic fibers 604, 605. FIG. 17a shows a refractive side firing configuration which transmits light to and receives light emitted by the tissue of interest. FIG. 17b shows a reflective coating side firing configuration. FIG. 17c shows a reflective attachment side fire configuration. FIG. 17d shows a mechanical bending front face firing configuration. FIG. 17e shows a front face firing configuration. Generally, side firing optic fibers can be readily self-manufactured, but are also commercially available from companies such as Ceramptec of East Longmeadow, Mass. Side firing optic fibers can be differentiated from front face firing optic fibers as described hereinafter. First, light enters and exits the side of optic fibers 604, 605 with respect to the fiber optic axis. This can be accomplished through two known methods, refractive and reflective. Refractively, no mirror-like coating are used to bend the light out the side of the optic fiber 604, 605. Specifically, it is the interaction between the index of refraction of the optic fiber 604, 605 core material and that of air. There is a "critical angle" 1702 to which the fiber 604, 605 is polished so that light leaving/entering out the side occurs in an optimal (most efficient—92%) fashion as illustrated in FIG. 17a. For the reflective method, the "critical angle" 1704 is not so critical to ensure that the light leaves out the side in the most efficient manner. The fibers 604, 605 are still polished at an angle 1704, but the back side of the polished area is coated with a reflective material 1706. This forces light that would have leaked out through the polished surface (believed to be approximately 8%) down out the side 1708 as illustrated in FIG. 17b. There is a subgroup of the reflective approach. This involves no angle polishing of fibers, so the light exits in the normal fashion, but there is an extension 1710 mechanically attached to the end of the fiber 604, 605. This extension 1710 has a mirror 1712 at its end which reflects the light exiting the fiber 604, 605 down to the side 1708, as illustrated in FIG. 17c. Front face firing assemblies, such as those depicted in FIGS. 17d and 17e, cannot lie flat on the skin because of the fixturing necessary to hold the fibers 604, 605 in place. Second, illumination/collection of light takes place with the fibers 604, 605 parallel to the tissue of interest. Third, effective emitting aperture is approximately 45% larger due to elliptical geometry of the polished or reflective surface.

Because of the aforementioned stated advantages of side firing optic fibers 604, 605, there are several functional performance advantages side firing fibers have as a result. These advantages can be summarized as follows: Side firing fiber assemblies have a low profile because the light exits/ enters the fiber from the side. This allows the fibers 604, 605 to be laid directly on the surface of the skin 1510, thereby allowing the fibers 604, 605 to be firmly secured in place.

Side firing fiber assemblies do not require the fibers 604, 605 to be bent, and therefore have a higher transmission efficiency over mechanically bent front face firing fibers. When light encounters a bend in an optic fiber 604, 605, a fraction of it is diverted from propagating down the remaining portion of the fiber 604, 605 and hence that fraction is lost. Fibers incur these bending losses due to a phenomena called "mode stripping" . Bends in a fiber effectively shorten the path for light that is traveling at the outer edges of the fiber core. When this occurs, this light propagates into the fiber cladding, and then is lost to free space outside the fiber assembly. Any losses incurred must be made up by increasing the intensity of the illumination source as described hereinbefore. This increases the power consumption of the system and generates more waste heat which then affects the performance of the spectrometer array 1504. Mechanical bending front face firing assemblies require bending the fibers 604, 605 in order to make the corner and contact the skin 1510.

Generally, side firing fiber assemblies have a higher reliability than mechanical bending front face firing fiber assemblies due to the lack of bend stresses. Optical fibers generally include a silica core. As the fiber is bent, the silica incurs microcracks that ultimately shorten the life of the fiber by creating a fracture which then prohibits light transmission. Since side firing assemblies are not configured in a manner which requires the fibers to be bent, their reliability is inherently higher than assemblies that require bending of fibers.

Side firing assemblies broadcast the light into a larger volume of tissue and likewise receive from more as well due to the elliptical face of the fiber, as described hereinbefore. With light being collected from a larger volume of tissue that had been interrogated, it has traveled a longer path and thereby had the opportunity to increase the sought after physiological signals as opposed to being lost, or not penetrating as far and coming back as noise. Transmission/ reception of light to/from an increased tissue volume in side firing assemblies is also due to the increase of the maximum angle at which the fibers can emit/gather light. This is due to the difference in geometry of the fiber faces. The elliptical face of the side firing fiber is 45% larger than the circular faces of the mechanical bending front face firing and front face firing fiber assemblies. This increase in face size allows the side firing assemblies to transmit/collect more useful light over a larger area which translates to more signal for the same power level. The power density is therefore reduced with sidefiring optical fibers.

In view of the foregoing, it believed that the optic fiber embodiments illustrated in FIGS. 17a, 17b and 17c can provide additional benefits when used with the present inventive system and to practice the present inventive method of measuring chromophore concentration levels within a blood-containing tissue.

Figure 18:
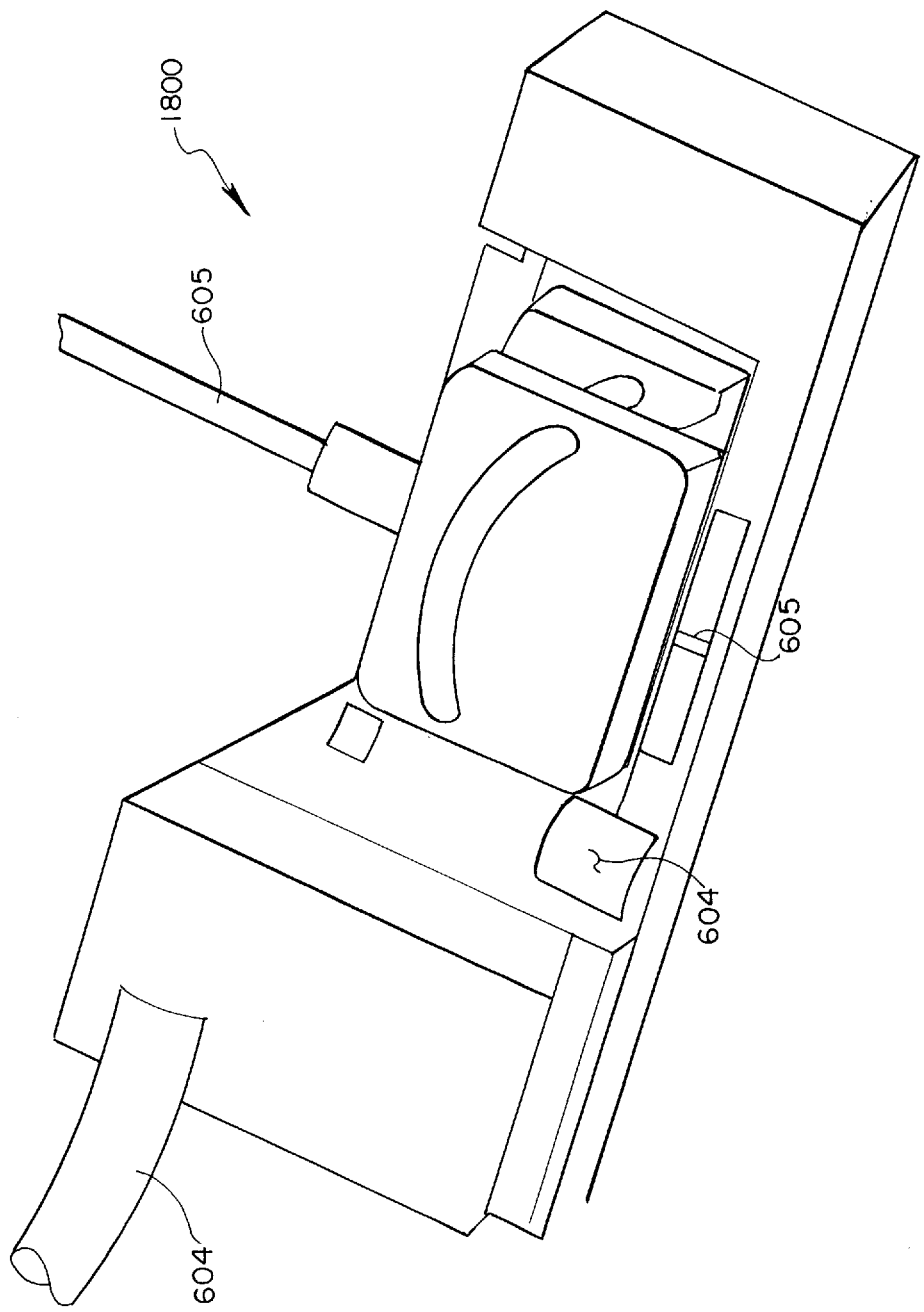
FIG. 18 illustrates one preferred embodiment for an adjustable spacing probe in which the send and receive optical fibers can be moved linearly and/or angularly with respect to each other, and which is suitable for use with the present inventive measurement system.

Turning to FIG. 18, an adjustable spacing probe 1800, suitable for use with the present inventive system is illustrated. Probe 1800 is useful to accomplish variable depth chromophore sampling measurements within a tissue and includes send and receive optic fibers 604, 605 that can be moved linearly and/or angularly with respect to each other. Since the depth of tissue sampled (optical path) is generally dependent upon the distance between illumination and detection fibers 604, 605 and to a smaller extent the angle between the fibers 604, 605, a probe tip that provides adjustment of these parameters allows one to sample different tissue depths within the same probe design.

In cases where the preferred measurement site (i.e. muscle layer) is beneath a layer of non-interest (i.e. skin and fat) it would be necessary to adjust the probe fiber 604, 605 spacing and/or angle in order to accommodate the wide variations between sample sites (i.e. varying fat thickness between patients). Therefore, it will readily be apparent that making probe adjustments based upon the surface layer thickness could be a means of removing surface layer bias (amount of signal from shallow tissue) from chromophore measurements.

Figure 19:
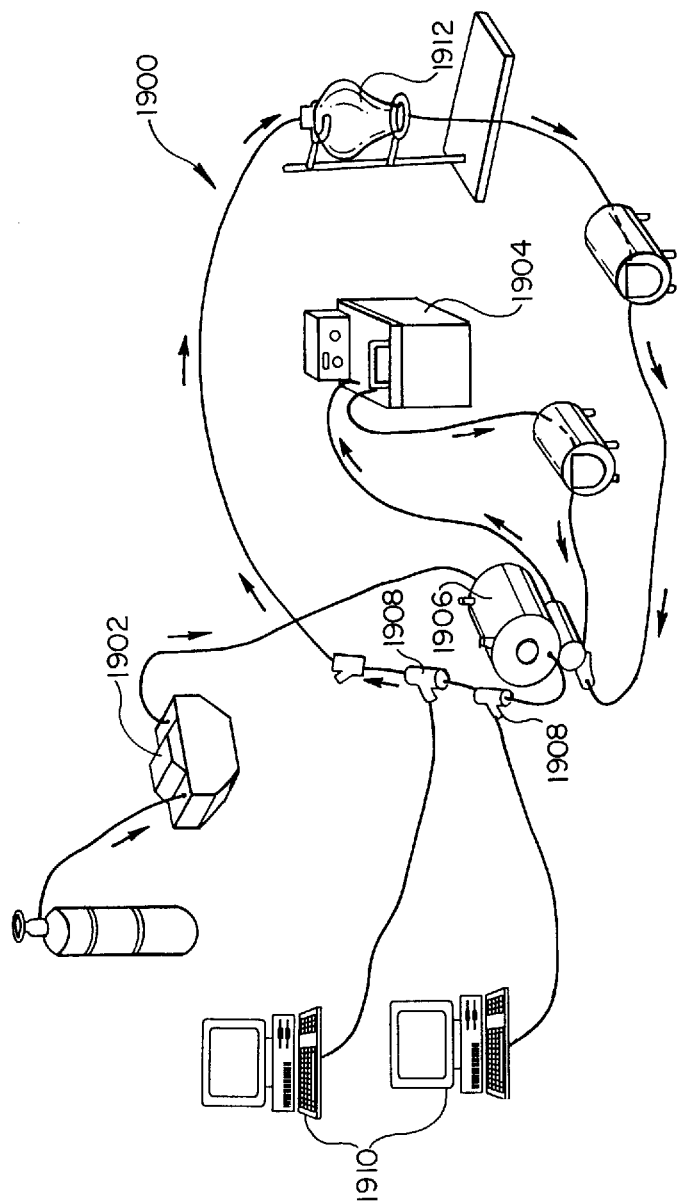
FIG. 19 illustrates one preferred embodiment of a blood flow circuit designed to provide a chromophore measurement environment that mimics chromophore states within tissue to establish algorithms that relate to quantification of predetermined chromophores within the tissue.

Turning to FIG. 19, a blood flow system 1900 which provides a hemoglobin measurement environment that mimics hemoglobin states within tissue having physiological characteristic observed in blood-containing tissue is illustrated. Blood flow measurement systems similar to that illustrated in FIG. 19 are generally well known to those skilled in the art. The operation of specific blood flow measurement apparatus are also well described in the known art, and therefore, a detailed description of particular devices, i.e. blood pump, blood reservoir, water pump, etc., will not be discussed herein to preserve brevity and clarity of the present inventive system and method for which a more detailed description now follows.

As stated hereinbefore, actual concentrations of a particular tissue chromophore with respect to a different but related tissue chromophore are measured using the present method and apparatus. Quantifying such measurements requires that specific algorithms be developed, i.e. algorithms that relate to quantification of hemoglobins within tissue are developed using empirical spectral measurements taken from the blood flow system 1900. Specifically, the blood flow system 1900 is first primed with whole blood (non-lysed red blood cells) which provides sufficient scattering to allow measurements with a reflectance probe such as those described in detail hereinbefore with reference to FIGS. 7, 8, 9, 10, 11, 12, 13, 17 and 18. Using the various devices, i.e. humidifier 1902, water bath 1904, membrane oxygenator 1906, blood reservoir 1912, and related peripheral devices shown in the blood flow system 1900, the temperature, pH, hemoglobin concentration and % oxyhemoglobin are first adjusted to reflect conditions that can occur within tissue having physiological characteristics exhibited by blood-containing tissue (tissue perfused with blood). For example, the sample blood is heated to 37° C.+/–0.5° C. by circulating water through a heat exchanger within a water bath 1904. The temperature is monitored with a thermocouple (not shown) positioned near the measurement flow cells 1908. A Fisher Scientific pH probe (also not shown) is placed in a blood reservoir 1912 to obtain blood sample pH measurements throughout each series of blood system 1900 measurements. Flow cells 1908 are used to interface biospectrometers 1910 to the hemoglobin environment established within the blood flow system 1900. The flow cells 1908 can be configured in any satisfactory manner to provide fixturing to interface the biospectrometers 1910 to the blood flow environment, so long as the flow cells 1908 provide a chamber that is opaque to ambient light, a volume space that minimizes light reflection from the chamber sidewalls of the flow cells 1908, and are constructed of a blood compatible material that is substantially spectrally flat in the wavelength region of interest. In cases where the optical path of the light includes reflections from the chamber sidewalls of the flow cells 1908, the spectrally flat material minimizes spectral shape bias from the chamber sidewalls of the flow cells 1908.

Figure 20:
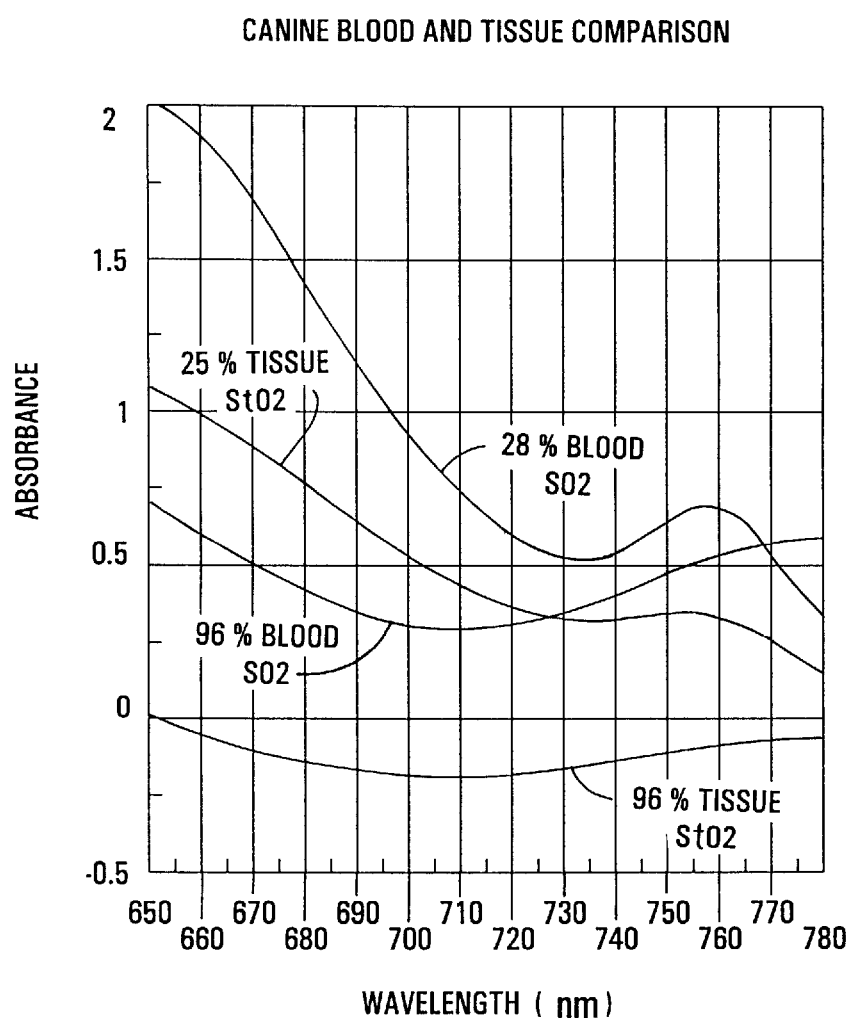
FIG. 20 is a comparison of an absorbance spectra over a spectral region of interest for a predetermined chromophore measurement obtained from within an in vivo measurement environment as it relates to a measurement obtained (in vitro) from within the blood flow circuit depicted in FIG. 19.
Figure 21:
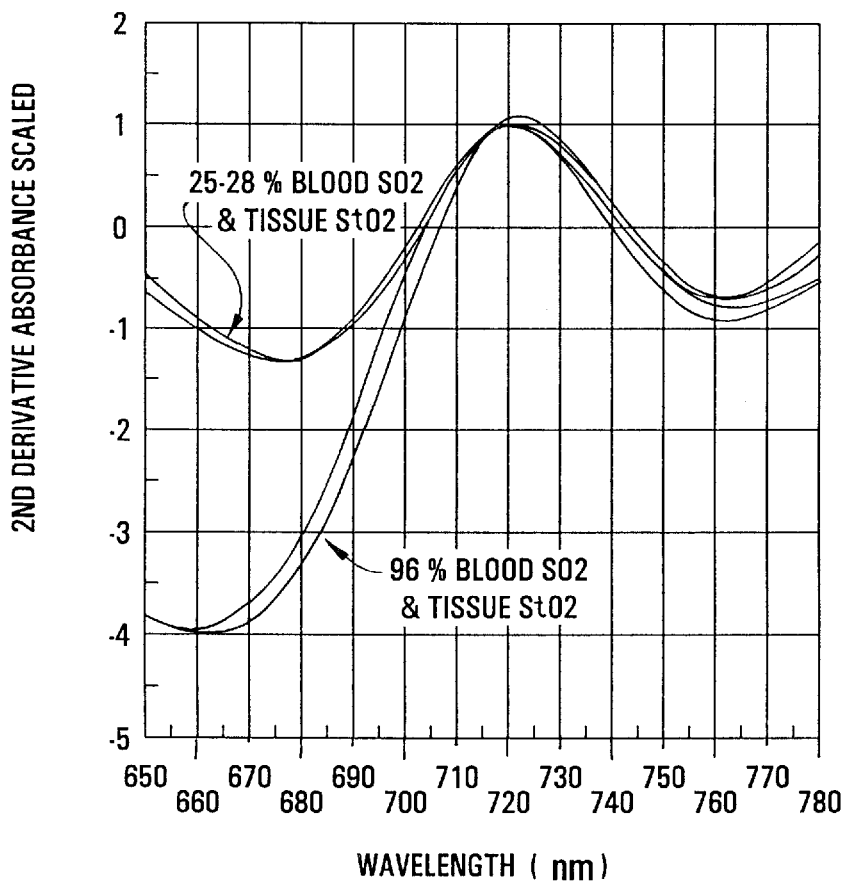
FIG. 21 is a graph which illustrates a second derivative absorbance spectra based upon the measured absorbance spectra depicted in FIG. 20.

Turning now to FIGS. 20 and 21, a comparison of absorbance spectrums measured in vitro with the blood flow system 1900 with absorbance spectrums obtained in vivo from canine tissue are illustrated. Specifically, an in vivo measurement environment (standard measurements made with use of commercially available co-oximeters from companies such as Instrumentation Laboratory of Lexington, Massachusetts and Ciba Corning Diagnostics Corp. of Medfield, Mass.) was provided to verify the accuracy and/or precision of the tissue chromophore (i.e. hemoglobin) measurement system 1900 with respect to an accepted standard method of obtaining hemoglobin measurements. In this manner, it then becomes possible to develop a predictive mathematical model over the spectral region of interest such that actual tissue chromophore concentrations can be determined with a high level of accuracy. The procedure for developing the proper mathematical model can generally be described as one in which the objective is to observe the relationship between hemoglobin oxygen saturation levels found in a sample tissue as measured non-invasively (in vitro) by the present blood flow system 1900 depicted in FIG. 19, and hemoglobin oxygen saturation levels found in the sample tissue as measured (in vivo) by a commercially available co-oximeter. Co-oximeters and their methods of use have long been known to those skilled in the art of chromophore measurement, and so details relating to use of co-oximeters to measure hemoglobin oxygen saturation levels will not be discussed herein. Specifically, the oxygen saturation is varied and measured in predetermined increments over a wide range, i.e. preferably 0%–100% total hemoglobin levels, and over a spectral region of interest, i.e. 600 nm–900 nm, for each total hemoglobin level, thereby allowing initial comparisons to be made between measurements made using the blood flow system 1900 and measurements made using a co-oximeter. In this manner the measurement apparatus, shown as 1500 in FIG. 15, can be calibrated, via an algorithm incorporating the aforesaid predictive mathematical model which is determined as described hereinafter in detail below with reference to FIGS. 22 and 24.

Figure 22:
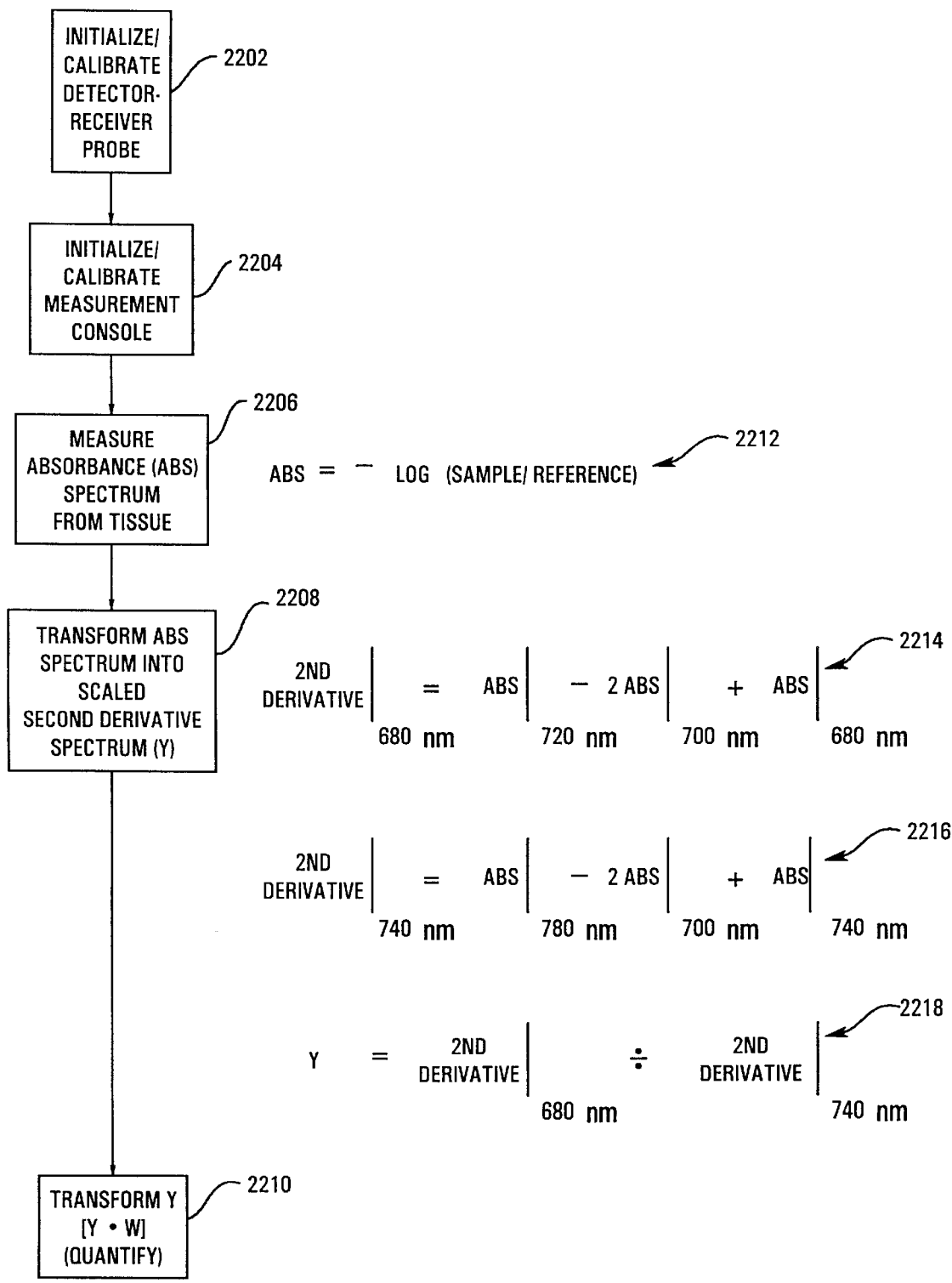
FIG. 22 is a flow chart depicting one preferred method for quantifying a relative concentration of a first predetermined tissue chromophore with respect to a second predetermined tissue chromophore suitable for implementation with the present measurement system.

Blood flow system 1900 is first primed 2402 with whole blood as stated above, to create chromophore conditions that mimic the intended use environment for the measurement system 1500. Next, a light reference is measured 2404 and the resultant spectrum is saved 2406 to the measurement system storage device (shown as 1552 in FIG. 15), i.e. disk drive, RAM, PROM, tape, or other appropriate memory means. Following the light reference measurement data storage 2406, an attenuation spectrum is measured 2408 for the whole blood sample at its initial desired hematocrit level and the associated data (wavelength vs. signal intensity) is also saved 2410 to the measurement system storage device, shown as 1552 in FIG. 15. The data associated with each light reference spectrum and attenuation spectrum measurement is assigned a respective and distinctive file name 2412 which is traceable to the specific chromophore measurement condition. At each aforesaid respective chromophore condition, a measurement of the actual chromophore condition is also recorded using an accepted standard of measurement 2414 (i.e., a 2 cc blood sample is drawn from the blood flow system 1900 and injected into a co-oximeter device which outputs a value for oxyhemoglobin relative to total hemoglobin). The foregoing steps are preferably completed over the course of several experimental runs 2416, thereby preferably obtaining hundreds of tissue attenuation spectra with corresponding reference spectra over a diverse measurement range (0% to 100% $SO_2$ at numerous total hemoglobin concentrations (i.e., 5 g/dl to 15 g/dl, where g/dl =grams per deciliter), represented by block 2430 in FIG. 24. The aforesaid spectrum measurement files are subsequently imported 2418 into a commercially available spreadsheet, e.g. Lotus 123®, which performs absorbance 2212, second derivative 2214, 2216 and second derivative scaled 2218 manipulations 2420 of the imported spectrum file data, such as illustrated in FIG. 22. The second derivative scaled 2218 data at a preselected wavelength (i.e. 680 nm), for each specific spectrum file are then imported to a new spreadsheet 2422. The aforesaid chromophore standard measured values obtained via co-oximeter measurements are aligned in the new spreadsheet with the corresponding filename and spectrum file values, shown as 2424 in FIG. 24. The following Table I illustrates a typical alignment for a series of standard values and corresponding file spectrum values at a preselected wavelength of 680 nm.

TABLE I

| FILENAME | STANDARD VALUE | FILE SPECTRUM VALUE (680 nm) |
| --- | --- | --- |
| May30__002.ssm | 95% | −4.25 |
| May30__003.ssm | 50% | −2.10 |
| May31__002.ssm | 0% | −1.25 |

With reference to the foregoing, a calibration data set that relates a scaled second derivative spectrum value to a quantified chromophore condition over a diverse measurement range can be determined. It is readily apparent a predictive mathematical model can be developed 2426, 2428 from the calibration data set and used to associate an inputted tissue spectral value to a predicted estimate of the chromophore condition for a specific chromophore.

One preferred method of forming the predictive mathematical model is to input the second derivative scaled values (Inputs) and their corresponding standard measurement values (Patterns) into a standard software package for creating a neural network algorithm 2426 (e.g., Brainmaker Professional® commercially available from California Scientific Software). The resultant algorithm is a matrix of weighting factors which relate the spectral input to a predicted output. The weighting factors are optimized so that the average residual error of the model (predicted value minus actual value at known measurement conditions) is minimized.

Another preferred and alternative method of forming the predictive mathematical model is to input the scaled second derivative variables with associated transformations (Independent Variable) and their corresponding standard measurements (Dependent Variable) into a standard software package capable of performing a multiple regression analysis 2428 (Quatro Pro® or Lotus 123®, for example). The following Table II exemplifies various dependent and independent variables.

TABLE II

| Dependent Variable | Independent Variables |
| --- | --- |
| Y | X, SquareRoot(X), Log(X), $X^2$, 1/X, $1/X^3$, etc. | where Y = standard chromophore measurement, and X = measured spectral value.

Use of this alternative modeling method requires that combinations of various X value transformations be selected in a manner such that the average residual error of the model is minimized. For example, only those transformations of X that significantly affect the model residual error (significant weighting coefficients) are included in the algorithm model. The predictive mathematical model which has been developed is then programmed into the measurement system computer (shown as 1550 in FIG. 15) to provide real-time conversions of tissue spectral values (i.e., 680 nm scaled second derivative absorbance) into displayed quantified values (i.e., % chromophore ratio).

Turning now to FIG. 22, a flow chart is illustrated which shows the specific methodology used by the present inventive apparatus to measure and determine a concentration of a first chromophore with respect to a total concentration of a second chromophore within a predetermined tissue of interest. As stated hereinbefore, the present innovation is a measurement system and method for quantifying relative concentrations of tissue chromophores. Examples of chromophores that the innovation could quantify would include % oxyhemoglobin relative to total hemoglobin concentration, % oxycytochrome(s) relative to total cytochrome(s) concentration and/or % total hemoglobin relative to total sampled tissue volume. The present invention is not so limited however, and it will be appreciated by those skilled the art that other chromophore concentrations may also be quantified using the present inventive method and apparatus.

In summation, the innovative technologies that define the present inventive chromophore measurement system have been categorized herein and throughout with regard to calibration methodology, probe and monitor design, and test methods/apparatus. A calibration technique has been described in detail that allows quantification of tissue hemoglobin chromophores that involves an isolated blood flow system design, shown as 1900 in FIG. 19, in which the second derivative reflectance spectra of hemoglobin at varying degrees of hemoglobin conditions are characterized. The transformation of the absorbance spectra into second derivative units provides an in vitro calibration set that correlates with in vivo measurements. Ratioing of second derivative spectral features allows measurements that are insensitive to varying optical pathlength (probe spacing designs) and changes in total chromophore concentration. Reference measurement and probe/detector alignment calibration methodologies are two important innovations that facilitate the measurement of accurate tissue absorbance spectra through a fiber optic probe.

Fiber optic probes, shown in FIGS. 7–13 and 17–18, include tissue interface tips which configure the send and receive optical fibers 604, 605 and are constructed of a material that minimizes measurement errors due to fluorescing and backscatter caused by light reflections. The connector 1600 that interfaces the send and receive optical fibers 604, 605 to the detection monitor 1502 is designed in a manner, illustrated in FIG. 16, which maximizes the available tissue signal. Side firing optical fiber designs have been illustrated in FIGS. 17a,b,c which provide a means of minimizing the probe 602, 1100, 1200 tip profile and an adjustable spacing probe design 1800 allows chromophore measurements at varying depths within the tissue of interest.

Figure 24:
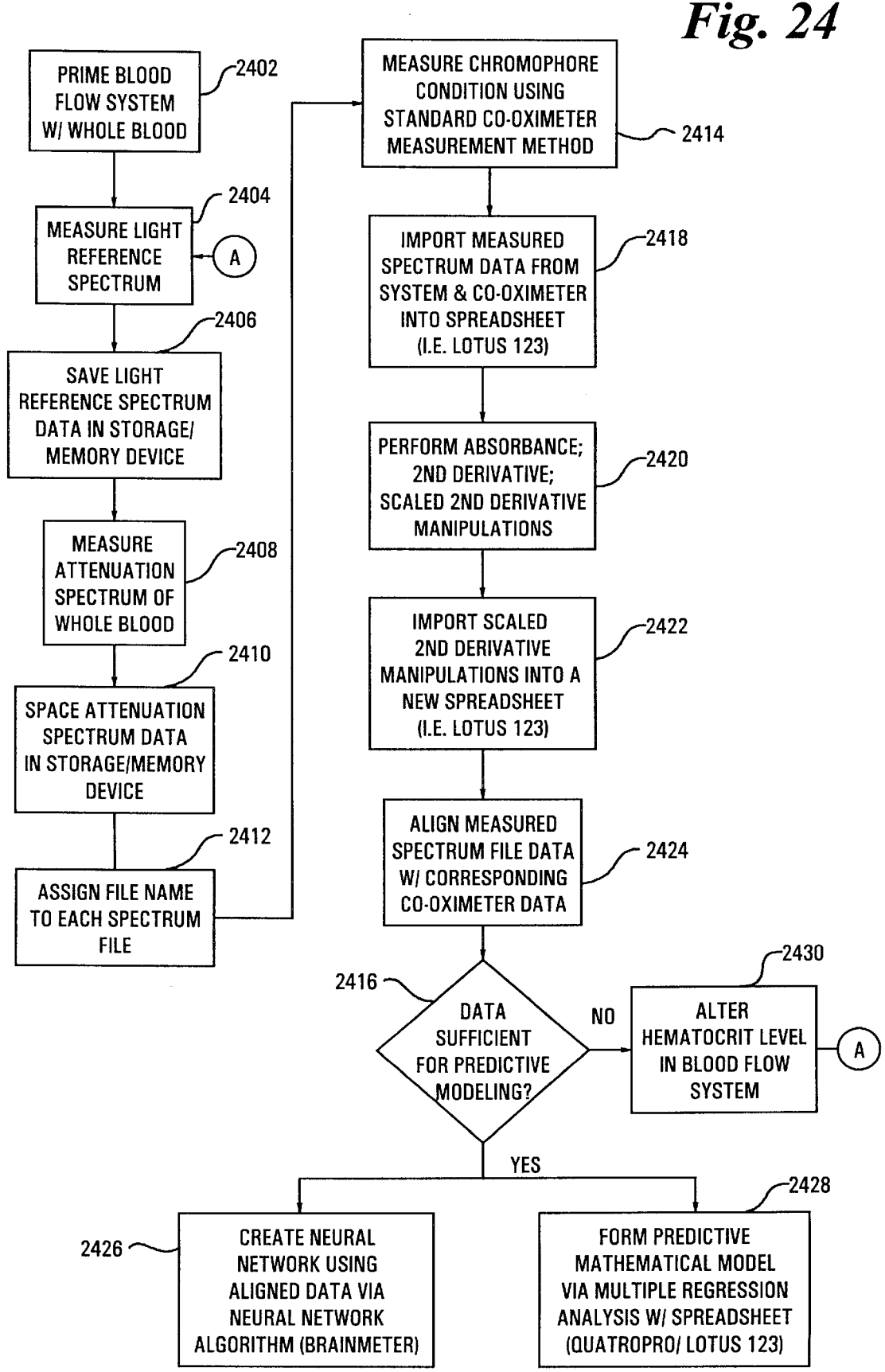
FIG. 24 is a flow chart illustrating one preferred method for constructing a predictive mathematical model for use in quantifying a relative concentration of a first predetermined tissue chromophore with respect to a second predetermined tissue chromophore suitable for use by the present measurement system.

The monitor 1502 design includes software methods, illustrated in FIGS. 22, 24 that accurately transform the tissue spectral characteristics into a quantifiable output signal via a computer 1550. These software methods can now be summarized with reference to FIG. 22. Looking again at FIG. 22, and particularly at block 2202, the present inventive process begins by first calibrating the detector/receive probe 602, 1100, 1200 within a reference and calibration canister 600 as described in detail hereinbefore. Where the pixel wavelength calibration is variant between detectors and non-evenly incremented within a detector, an interpolation algorithm is performed on each attenuation spectra in order to obtain a consistent wavelength absorbance measurement from detector to detector. Where the pixel wavelength calibration is variant between probe connections to a given detector, the detector pixel calibration coefficients are adjusted with each probe connection by means of the detector wavelength calibration canister 600. Simultaneously or at any other time prior to or following probe 602 calibration, the measurement console 1502 is also calibrated as shown in block 2204. In order to maintain an adequate signal to noise ratio for each measurement and to avoid saturation of the detector array 1504, the detector 1504 integration time within the measurement console 1502 is automatically adjusted whenever a signal falls below or above a predetermined limit to ensure that the desired signal is accurately being detected and measured. To minimize dark current bias errors associated with dark current drift and/or integration time changes, the dark current is automatically measured whenever an integration time change occurs and/or a predetermined time limit is exceeded. A periodic dark current measurement between sample measurements is performed to minimize errors from ambient light being included in the sample measurements. Methods for implementing the aforementioned calibration processes generally are done through software routines using programming techniques and algorithms found in commercially available software textbooks and training manuals, e.g., Nyquist sampling, watchdog timer routines, etc., and so details of the specific calibration methods used with the present invention will not be discussed herein to preserve clarity and brevity. Most preferably, the software is coded so that tissue spectral characteristics can be input into a neural network 2210, 2426 or other prediction algorithm (e.g. multiple regression analysis routine 2428) for displaying measured values in real-time as discussed in considerable detail hereinbefore. Following completion of the foregoing calibration routines, a probe 602, 100, 1200 (or other suitable means) is used to irradiate a predetermined tissue and detect light emitted from the tissue. An absorbance spectrum is then determined in block 2206 by the present inventive system 1500 illustrated in FIG. 15, which can, but need not include at least one probe 602, 1100, 1200 in combination with a monitoring console 1502 optionally incorporating side firing optic fibers such as those illustrated in FIGS. 17a,b,c. A spectrometer detector 1504 transforms the light signal emitted from the tissue into a multiple wavelength spectrum, FIG. 1. Performing spectral measurements, depicted in block 2208 on at least four individual wavelengths, illustrated in FIG. 22, is required to perform ratio measurements of two individual second derivative features, shown as Y in FIG. 22. Regarding the aforesaid spectral measurements, the light source assembly 1400 is designed to provide continuous wave stable illumination of the tissue and provides maximum signal intensity with minimal heat generation, as stated hereinbefore.

One embodiment of the present apparatus and method includes application of an isolated blood flow system 1900 that allows measurement of the reflected and/or attenuated spectral features of whole blood. A related in vivo canine protocol provides a method for verifying correlation between the in vitro (blood system 1900) and in vivo (living tissue) measurement, and for determining correlation and/or weighting coefficients (W) for quantifying the aforesaid second derivative spectral features, as illustrated in block 2210. Preferably, a neural network 2210 selftest feature is used to measure a known spectral standard (real-time) and output an appropriate error message if the measured output is not within acceptable limits. This insures that the systems (i.e. probe, alignment, reference measurement, dark current measurement, signal intensity, etc.) are working properly.

From the foregoing detailed descriptions of particular embodiments of the invention, it will be apparent that a flexible and easy to use system and method have been disclosed which is provided with the capability of measuring the concentration of a first tissue chromophore with respect to a total concentration of a second tissue chromophore within a tissue having physiological characteristics of blood-containing tissue, where the measurements are substantially robust to changes in relative or total chromophore concentrations or optical pathlengths, non-linear spectral contributors, and/or scattering effects. While the invention has been described above in connection with the particular embodiments and examples, one skilled in the art will appreciate that the invention is not necessarily so limited. It will thus be understood that numerous other embodiments, examples, uses, modifications of, and departures from the teachings disclosed may be made, without departing from the scope of the present invention as claimed herein, an example being application of the foregoing apparatus and methods to measure chromophore data in tissue which is not perfused with blood or otherwise exhibiting characteristics observed in blood-containing tissue. The present invention can also be practiced without the aid of light probes, for example. It is only necessary that a particular tissue being interrogated be irradiated. The particular apparatus used to irradiate the tissue and measure respective attenuation characteristics for the irradiated tissue are not limited to the embodiments disclosed herein. Any apparatus capable of irradiating a tissue at a minimum of four distinct wavelengths and measuring the respective tissue chromophore characteristics at those distinct wavelengths may be used so long as the methodology described in detail hereinbefore can be utilized to extract the necessary data to practice the present invention.

We claim:

1. A measurement system for determining a relative concentration of a first form of a chromophore in a tissue sample, said chromophore comprising at least a first form and a second form, comprising:
   (a) means for irradiating said tissue sample with light at a plurality of wavelengths within a wavelength range within which the first and second forms of the chromophore provide an overlapping spectral response, such that spectral data is emitted from said tissue;
   (b) means for detecting the spectral data emitted from said tissue;
   (c) means for determining a first 2d derivative spectrum value of the spectral data at a first wavelength within said wavelength range at which the first 2d derivative spectrum value varies with the relative concentration of the first form of the chromophore;
   (d) means for determining a second 2d derivative spectrum value of the spectral data at a second wavelength within said wavelength range at which the first 2d derivative spectrum value varies with the relative concentration of the first form of the chromophore;
   (e) means for deriving a scaled, 2d derivative spectrum value from information comprising the first and second 2d derivative spectrum values; and
   (f) means for storing a correlation which provides the relative chromophore concentration as a function of the scaled, 2d derivative spectrum value; and (g) means for determining the relative concentration of the first form of the chromophore in the tissue sample from information comprising the scaled, 2d derivative spectrum value and the correlation.

2. The measurement system of claim 1 wherein said means for irradiating said predetermined tissue with light comprises a continuous wave, broad bandwidth light source.

3. The measurement system of claim 2 wherein said means for irradiating said predetermined tissue with light further comprises a light transmission probe having at least one optical fiber for passing light emitted by said continuous wave, broad bandwidth light source to said predetermined tissue.

4. The measurement system of claim 3 wherein said light transmission probe is comprised of a nonfluorescing material.

5. The measurement system of claim 4 wherein said light transmission probe is further comprised of a spectrally flat material over a spectral region of interest.

6. The measurement system of claim 5 wherein at least one end of said at least one optical fiber is configured as a side-firing optical fiber.

7. The measurement system of claim 4 wherein the probe includes an opaque face.

8. The measurement system of claim 1 wherein said means for irradiating said predetermined tissue comprises an infra-red (IR) filter device to eliminate passage of IR radiation to said predetermined tissue.

9. The measurement system of claim 1 wherein said means for detecting the spectral data emitted from said predetermined tissue comprises a wavelength sensitive detector.

10. The measurement system of claim 9 wherein said wavelength sensitive signal detector comprises a linear diode array spectrometer.

11. The measurement system of claim 9 wherein said wavelength sensitive signal detector comprises a linear capacitor array spectrometer.

12. The measurement system of claim 9 wherein said means for detecting the spectral data emitted from said predetermined tissue further comprises a light receive probe having at least one optical fiber for passing said light emitted from said predetermined tissue to said signal detector.

13. The measurement system of claim 1 wherein said means for detecting the spectral data emitted from predetermined tissue comprises a high pass filtering device adapted to cut off passage of said light signals emitted from said predetermined tissue at wavelengths below approximately 500 nanometers.

14. The measurement system of claim 1 wherein said means for storing said correlation is a computer memory.

15. The measurement system of claim 1 wherein said means for determining said relative concentration is a computer.

16. A method of measuring a relative concentration of a first form of a chromophore in a tissue sample, said chromophore comprising at least a first form and a second form, comprising the steps of:
   (a) obtaining spectral data for said tissue sample over a plurality of wavelengths within a wavelength range within which the first and second forms of the chromophore provide an overlapping spectral response to irradiation with spectroscopic radiation;
   (b) determining a first 2d derivative spectrum value of the spectral data at a first wavelength within said wavelength range at which the first 2d derivative spectrum value varies with the relative concentration of the first form of the chromophore;

(c) determining a second 2d derivative spectrum value of the spectral data at a second wavelength within said wavelength range at which the first 2d derivative spectrum value varies with the relative concentration of the first for-m of the chromophore;

(d) deriving a scaled, 2d derivative spectrum value from information comprising the first and second 2d derivative spectrum values;

(e) determining the relative concentration of the first form of the chromophore in the tissue sample from information comprising the scaled, 2d derivative spectrum value and a correlation which provides the relative concentration of the first form of the chromophore as a function of the scaled, 2d derivative spectrum value.

17. The method of claim 16, wherein the spectral data is obtained from the tissue sample in vivo.

18. The method of claim 16, wherein the scaled, 2d derivative spectrum value is a ratio between said first and second 2d derivative spectrum values.

19. The method of claim 16, wherein step (a) comprises irradiating the tissue sample with near infrared radiation in order to obtain the spectral response.

20. The method of claim 16, wherein said wavelength range is from about 600 nm to about 900 nm.

21. The method of claim 16, wherein step (a) comprises the steps of:
  (i) providing a probe having a tissue sample interface surface for irradiating the tissue sample with the spectroscopic radiation and for receiving light emitted from the tissue sample in response to said irradiation;
  (ii) providing a light source assembly for generating the spectroscopic radiation, said light source assembly comprising:
    (1) a light source; and
    (2) at least one send optical fiber optically coupling the light source to the tissue interface surface of the probe, wherein the send optical fiber has a light entry region disposed proximal to the light source for receiving the spectroscopic radiation and a light exit region coupled to the tissue sample interface surface of the probe for emitting the spectroscopic radiation onto the tissue sample;
  (iii) irradiating the tissue sample with spectroscopic radiation transported to the tissue sample through the send optical fiber.

22. The method of claim 21, wherein the spectroscopic radiation is near infrared radiation.

23. The method of claim 21, wherein the tissue sample interface surface of the probe comprises a spectrally flat surface portion proximal to the send optical fiber.

24. The method of claim 21, wherein the tissue sample interface surface of the probe comprises polyphenylsulfone.

25. The method of claim 21, wherein the tissue sample interface surface of the probe comprises a reflective portion to amplify a shallow depth measurement of the tissue sample.

26. The method of claim 21, wherein the tissue sample interface surface of the probe comprises a non-reflective surface portion.

27. The method of claim 21, wherein the probe further comprises an antimicrobial black nylon fabric disposed proximal to the tissue sample interface surface of the probe.

28. The method of claim 21, wherein the probe further comprises an infrared cutoff filter disposed proximal to the tissue sample interface surface.

29. The method of claim 21, wherein the light source assembly further comprises a light source shroud for focusing the spectroscopic radiation emitted by the light source onto a focal area, and wherein the light entry region of said at least one send optical fiber is disposed at the focal area.

30. The method of claim 21, wherein the light source comprises a continuous wave broad bandwidth lamp capable of generating a spectrum sufficient to cover said plurality of wavelengths.

31. The method of claim 21, wherein the light source comprises a plurality of narrow bandwidth lamps having overlapping spectrums sufficient to cover said plurality of wavelengths.

32. The method of claim 21, wherein the light source assembly further comprises an optical fiber feedback loop comprising:
  (i) a power sensor for sensing the output of the light source;
  (ii) at least one feedback optical fiber optically coupling the light source to the power sensor; and
  (iii) a control system interfaced with the light source and the power sensor such that the control system is capable of controllably adjusting the output of the light source in order to stabilize the amount of radiation emitted by the light source.

33. The method of claim 32, wherein the control system has a switching frequency substantially less than the thermal time constant of the light source.

34. The method of claim 16, wherein step (a) comprises the steps of:
  (i) providing a fiber optic probe comprising a tissue sample interface surface;
  (ii) providing at least one send optical fiber having a first region adapted for receiving the spectroscopic radiation from a light source and a second region coupled to the tissue sample interface surface of the probe for emitting the spectroscopic radiation onto the tissue sample;
  (iii) providing at least one receive optical fiber having a first region coupled to the tissue sample interface surface of the probe for receiving light emitted from the tissue sample in response to irradiation with the spectroscopic radiation and a second region adapted to be optically coupled to a spectroscopic detector;
  (iv) irradiating the tissue sample with spectroscopic radiation transported to the tissue sample through the send optical fiber; and
  (v) determining the spectral response of the tissue sample from information comprising the spectroscopic radiation transported to the spectroscopic detector through the receive optical fiber.

35. The method of claim 34, wherein the send and receive optical fibers are coupled to the probe with a side firing configuration.

36. The method of claim 34, wherein the spectroscopic radiation is near infrared radiation.

37. The method of claim 34, further comprising
  (i) using the fiber optic probe to obtain a reference spectrum; and
  (ii) deriving the scaled, 2d derivative spectrum value from information comprising the spectral response of the tissue sample and the reference spectrum.

38. The method of claim 37, wherein the step of using the fiber optic probe to obtain a reference spectrum comprises the steps of:
  (i) positioning at least the tissue sample interface surface of the probe into a container having a spectrally flat material inside the container, said probe being positioned in the container in a manner such that ambient light is excluded from the container;

(ii) irradiating the spectrally flat material with spectroscopic radiation transported to the container through the send optical fiber;

(iii) using the receive optical fiber to receive light emitted from the spectrally flat material responsive to the irradiation and to transport the emitted light to the spectroscopic detector; and (iv) determining the reference spectrum from information comprising the spectroscopic radiation emitted from the spectrally flat material and transported to the spectroscopic detector through the receive optical fiber.

39. The method of claim 37, further comprising the step of calibrating the fiber optic probe prior to obtaining the reference spectrum and prior to measuring the spectral response of the tissue sample.

40. The method of claim 39, wherein the step of calibrating the fiber optic probe comprises the steps of:

(i) positioning a filter in a canister having a spectrally flat material inside the container, wherein the filter is capable of emitting a spectral response comprising a plurality of spectral peaks at known wavelengths in response to irradiation with the spectroscopic radiation;

(ii) positioning at least the tissue sample interface surface of the probe into the container in a manner such that ambient light is excluded from the container;

(iii) irradiating the filter and spectrally flat material with spectroscopic radiation transported to the container through the send optical fiber;

(iv) using the receive optical fiber to receive light emitted from the filter and spectrally flat material responsive to the irradiation and to transport the emitted light to the spectroscopic detector; and (v) calibrating the probe from information comprising the emitted light transported from the container to the spectroscopic detector through the receive optical fiber.

41. The method of claim 6, wherein the scaled, 2d derivative spectrum value corresponds to a wavelength of the spectral response at which the slope of a scaled second derivative spectrum derived from the spectral response is substantially identical to the slope of a plurality of scaled, second derivative spectra obtained for a plurality of other tissue samples characterized by different relative concentrations of the chromophore.

42. The method of claim 16, wherein step (a) further comprises the steps of:

(i) transforming the spectral response into a second derivative spectrum;

(ii) providing a scaling factor for scaling the second derivative spectrum; and (iii) determining the scaled, 2d derivative spectrum value from information comprising the second derivative spectrum and the scaling factor.

43. The method of claim 42, wherein the scaling factor corresponds to the maximum amplitude value of the second derivative spectrum.

44. The method of claim 16, wherein the correlation is derived from scaled second derivative spectrum values obtained for a plurality of reference tissue samples and corresponding relative chromophore concentrations for the plurality of the reference tissue samples.

45. The method of claim 44, wherein the correlation is obtained by a method comprising the steps of:

(i) providing a plurality of the reference tissue samples, wherein said reference tissue samples are characterized by a plurality of different relative chromophore concentrations;

(ii) measuring the relative chromophore concentration of each of the reference tissue samples;

(iii) measuring the spectral response of each of the reference tissue samples over plurality of wavelengths within the wavelength range from 600 nm to 900 nm;

(iv) deriving a scaled, 2d derivative spectrum value for each of the reference tissue samples, wherein each of the scaled, 2d derivative spectrum values is obtained from information comprising the spectral data obtained for each reference tissue sample, respectively; and (v) developing the correlation from information comprising the measured relative concentrations and the corresponding scaled, 2d derivative spectrum values.

46. The method of claim 45, wherein the spectral response of each of the reference tissue samples is obtained in a blood flow measurement system.

47. A system for measuring a relative concentration of a first form of a chromophore in a tissue sample, said chromophore comprising at least a first form and a second form, comprising:

(a) a memory comprising data representative of a correlation which provides the relative concentration of the first form of the chromophore as a function of a scaled, 2d derivative spectrum value input, wherein the scaled second derivative value input is derived from a spectral response obtained from the tissue sample at a plurality of wavelengths within a wavelength range from 600 nm to 900 nm;

(b) a light source assembly for generating spectroscopic radiation for irradiating the tissue sample;

(c) a spectroscopic detector for detecting the spectral response emitted by the tissue sample responsive to irradiation with the spectroscopic radiation; and (d) a control system interfaced with the memory and the spectroscopic detector such that:

the control system generates the scaled, second derivative spectrum value of the tissue sample from information comprising the spectral response of the tissue sample; and (ii) the control system generates information representative of the relative concentration of the first form of the chromophore in the tissue sample from information comprising the scaled, second derivative spectrum value and the correlation provided in the memory.

48. The system of claim 47, wherein the scaled, 2d derivative spectrum value is obtained from the tissue sample in vivo.

49. The system of claim 47, wherein the spectroscopic radiation is near infrared radiation.

50. The system of claim 47, wherein the system further comprises a probe having a tissue sample interface surface for irradiating the tissue sample with the spectroscopic radiation and for receiving light emitted from the tissue sample in response to said irradiation; and wherein the system further comprises a light source assembly comprising:

(1) a light source for radiating the spectroscopic radiation; and (2) at least one send optical fiber optically coupling the light source to the tissue interface surface of the probe, wherein the send optical fiber has a light entry region disposed proximal to the light source for receiving the spectroscopic radiation and a light exit region coupled to the tissue sample interface surface of the probe for emitting the spectroscopic radiation onto the tissue sample.

51. The system of claim 50 wherein the spectroscopic radiation is near infrared radiation.

52. The system of claim 50, wherein the tissue sample interface surface of the probe comprises a spectrally flat surface portion.

53. The system of claim 50, wherein the tissue sample interface surface of the probe comprises polyphenylsulfone.

54. The system of claim 50, wherein the tissue sample interface surface of the probe comprises a reflective portion to amplify a shallow depth measurement of the tissue sample.

55. The system of claim 54, wherein the light source assembly further comprises a light source shroud for focusing the spectroscopic radiation emitted by the light source onto a focal area, and wherein the light entry region of said at least one send optical fiber is disposed at the focal area.

56. The system of claim 50, wherein the tissue sample interface surface of the probe comprises a non-reflective surface.

57. The system of claim 50, further comprising an antimicrobial black nylon fabric dispose proximal to the tissue sample interface surface of the probe.

58. The system of claim 50, wherein the probe further comprises an infrared cutoff filter dispose proximal to the tissue sample interface surface.

59. The system of claim 50, wherein the light source comprises a continuous wave broad bandwidth lamp capable of generating a spectrum sufficient to cover said plurality of wavelengths.

60. The system of claim 50, wherein the light source comprises a plurality of narrow bandwidth lamps having overlapping spectrums sufficient to cover said plurality of wavelengths.

61. The system of claim 50, wherein the light source assembly further comprises an optical fiber feedback loop comprising:
 (i) a power sensor for sensing the output of the light source;
 (ii) at least one feedback optical fiber optically coupling the light source to the power sensor; and wherein the control system is further interfaced with the light source and the power sensor such that the control system is capable of controllably adjusting the output of the light source in order to stabilize the amount of radiation emitted by the light source.

62. The system of claim 61, wherein the control system has a switching frequency substantially less than the thermal time constant of the light source.

63. The system of claim 50, further comprising at least one receive optical fiber having a first region coupled to the tissue sample interface surface of the probe and a second region coupled to the spectroscopic detector.

64. The system of claim 63, wherein the send and receive optical fibers are coupled to the probe with a side firing configuration.

65. The system of claim 63, further comprising a container having a spectrally flat material inside the container and an aperture adapted to receive the probe in a manner such that ambient light is excluded from the container and such that the probe is capable of irradiating the spectrally flat material with the spectroscopic radiation and receiving radiation reflected by said material responsive to irradiation.

66. The system of claim 65, wherein the system further comprises a filter disposed in the container, wherein the filter emits a spectral response comprising a plurality of spectral peaks at known wavelengths in response to irradiation with the spectroscopic radiation.

67. The system of claim 47, wherein the system further includes machine readable program instructions enabling the system to
 (i) actuate the light source assembly and the spectroscopic detector to obtain a spectral response of the tissue sample;
 (ii) transform the spectral response into a second derivative spectrum;
 (iii) provide a scaling factor for scaling the second derivative spectrum; and
 (iv) determine a scaled, 2d derivative spectrum value for the tissue sample from information comprising the second derivative spectrum and the scaling factor.

68. The system of claim 67, wherein the scaling factor corresponds to the maximum amplitude value of the second derivative spectrum.

* * * * *

UNITED STATES PATENT AND TRADEMARK OFFICE
CERTIFICATE OF CORRECTION

PATENT NO. : 5,879,294
DATED : March 9, 1999
INVENTOR(S) : Anderson et al.

It is certified that error appears in the above-identified patent and that said Letters Patent is hereby corrected as shown below:

Column 25, line 5, delete "for-m" and insert therefor --form--

Column 27, line 38, delete "6" and insert therefor --16--

Column 28, line 36, before the first occurrence of "the" insert --(i)--

Column 29, line 21, delete "dispose" and insert therefor --disposed--

Column 29, line 24, delete "dispose" and insert therefor --disposed--

Signed and Sealed this

Tenth Day of August, 1999

Attest:

Q. TODD DICKINSON

*Attesting Officer*  *Acting Commissioner of Patents and Trademarks*